United States Patent [19]
Witzel et al.

[11] Patent Number: 5,536,727
[45] Date of Patent: Jul. 16, 1996

[54] 17-ETHERS AND THIOETHERS OF 4-AZA-STEROIDS

[75] Inventors: Bruce E. Witzel, Westfield; Richard L. Tolman, Warren; Gary H. Rasmusson, Watchung; Raman K. Bakshi, Edison; Shu Shu Yang, Bridgewater, all of N.J.

[73] Assignee: Merck & Co., Inc., Rahway, N.J.

[21] Appl. No.: 338,572

[22] PCT Filed: May 19, 1993

[86] PCT No.: PCT/US93/04746

§ 371 Date: Nov. 17, 1994

§ 102(e) Date: Nov. 17, 1994

[87] PCT Pub. No.: WO93/23040

PCT Pub. Date: Nov. 25, 1993

Related U.S. Application Data

[63] Continuation-in-part of Ser. No. 886,031, May 20, 1992, abandoned.

[51] Int. Cl.⁶ .............................. A61K 31/58; C07J 73/00
[52] U.S. Cl. ................. 514/284; 546/77; 546/78
[58] Field of Search .............................. 514/284; 546/77, 546/78

[56] References Cited

U.S. PATENT DOCUMENTS

| | | | |
|---|---|---|---|
| 2,227,876 | 1/1941 | Bolt | 546/77 |
| 3,239,417 | 3/1966 | DiTullio et al. | 546/77 |
| 3,264,301 | 8/1966 | Doorenboos . | |
| 3,285,918 | 11/1966 | Doorenboos et al. . | |
| 4,139,619 | 2/1979 | Chidsey, III . | |
| 4,220,775 | 9/1980 | Rasmusson et al. | 546/77 |
| 4,317,817 | 3/1982 | Blohm et al. . | |
| 4,377,584 | 3/1983 | Rasmusson et al. | 546/77 |
| 4,596,812 | 6/1986 | Chidsey, III et al. . | |
| 4,732,897 | 3/1988 | Cainelli et al. . | |
| 4,760,071 | 7/1988 | Rasmusson et al. | 546/77 |
| 4,845,104 | 7/1989 | Carlin et al. . | |
| 4,859,681 | 8/1989 | Rasmusson et al. | 546/77 |
| 4,882,319 | 11/1989 | Holt et al. . | |
| 4,888,336 | 12/1989 | Holt et al. | 514/284 |
| 4,910,226 | 3/1990 | Holt et al. . | |
| 5,049,562 | 9/1991 | Rasmusson et al. | 514/284 |
| 5,110,939 | 5/1992 | Holt et al. | 548/250 |
| 5,116,983 | 5/1992 | Bhattacharya et al. | 546/77 |
| 5,120,742 | 6/1992 | Rasmusson et al. | 514/284 |
| 5,175,155 | 12/1992 | Juniewicz et al. | 514/284 |

FOREIGN PATENT DOCUMENTS

| | | |
|---|---|---|
| 970692 | 7/1975 | Canada . |
| 0004949 | 10/1979 | European Pat. Off. . |
| 0155096 | 9/1985 | European Pat. Off. . |
| 0200859 | 11/1986 | European Pat. Off. . |
| 0277002 | 6/1988 | European Pat. Off. . |
| 0289327 | 11/1988 | European Pat. Off. . |
| 0314199 | 5/1989 | European Pat. Off. . |
| 0343954 | 11/1989 | European Pat. Off. . |
| 0375344 | 6/1990 | European Pat. Off. . |
| 0375345 | 6/1990 | European Pat. Off. . |
| 0375347 | 6/1990 | European Pat. Off. . |
| 0375349 | 6/1990 | European Pat. Off. . |
| 1465544 | 11/1965 | France . |
| WO91/12261 | 8/1991 | WIPO . |

OTHER PUBLICATIONS

Endo., vol. 91, No. 2, pp. 427–437 (1972) by Neri, et al., "A Biological Profile of a Non–steroidal Antiandrogen, SCH 13521 . . . ".

Steroids, 14, 269–283(1969), by Nayfeh, et al., "Metabolism of Progesterone by Rat Testicular Homogenates–III".

Endo., vol. 92, p. 1216 (1973) by Voight & Hsia (See disclosure in Reference AP).

J. Pharm. Sci., 62, No. 4, pp. 638–640 (1973) by Doorenbos & Solomons, "Synthesis & Antimicrobial Properties of 17 Beta–Isopentyloxy–4–Aza–5 Alpha–Androstane and the 4–Methyl Derivative".

J. Pharm. Sci., 60, No. 8, pp. 1234–1235 (1971) by Doorenbos & Brown, "4.17 Alpha–Dimethyl–4–Aza–5 Alpha–Androstan–17 beta–ol Acetate & Related Azasteroids".

J. Pharm., 63, No. 4, pp. 620–622 (1974) by Doorenbos & Kim, "Synthesis & Evaluation of Antimicrobial Properties of Amidinoazaandrostanes and Guanidinoazaandrostanes".

J. Med. Chem. (1986) 29 (11): pp. 2298–3115 by Rasmusson, et al., "Aza Steroids: Structure–Activity Relationships. . . ".

Prostate (1986) 9(1): pp. 65–75 by Brooks, et al., "Prostatic Effects Induced in Dogs By . . . 5 alpha–Reductase Inhibitors".

Steroids (1986) 47 (1): pp. –19 by Brooks, et al., "5 Alpha–Reductase Inhibitory . . . Activities of Some 4–Aza–Steroids in the rat".

Endocr. (1985) 117 (2): pp. 571–579, by Liang, et al., "Species Differences in Prostatic Steroidal 5 Alpha–Reductases of Rat. Dog and Human".

J. Med. Chem. (1984) 27 (12): pp. 1690–1701, by Rasmusson, et al., "Azasteroids as Inhibitors of Rat Prostatic 5 alpha–reductase".

(List continued on next page.)

*Primary Examiner*—Donald G. Daus
*Attorney, Agent, or Firm*—Joanne M. Giesser; Catherine D. Fitch

[57] ABSTRACT

Compounds of Formula I

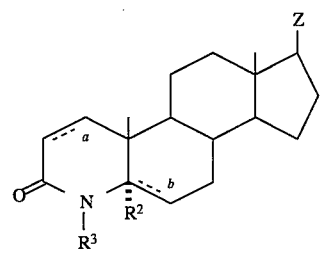

wherein Z contains an ether or thioether moeity, are inhibitors of the 5α-reductase enzyme and isozymes thereof. The compounds are useful for the treatment of hyperandrogenic disease conditions and diseases of the skin and scalp.

12 Claims, No Drawings

OTHER PUBLICATIONS

J. Org. Chem. (1981) vol. 46, No. 7, pp. 1442–1446, T. Back, et al., "N–Chloroazasteroids . . . ".

Chem. Abstracts, vol. 95, 109055j, by T. Liang, et al. "Inhibition of 5 Alpha–Receptor Binding . . . by a 4–Methyl–4–Aza–Steroid".

JNCI, vol. 74, No. 2, pp. 475–481 (Feb. 1985), by N. Kadohama, et al., "Retardation of Prostate Tumor Progression in the Noble Rat by 4–Methyl–4–Aza–Steroidal Inhibitors of 5 Alpha–Reductase".

The Prostate, vol. 10, pp. 189–197 (1987) by G. Andriole, et al., "The Effect of 4MA . . . on the Growth of . . . Human Tumors . . . ".

J. Endocr., vol. 57, pp. 111–121 (1973) by K. D. Bingham, et al., "The Metabolism of Testosterone by Human Male Scalp Skin".

Toxicol. Appl. Pharmacol., vol. 103, pp. 222–227 (1990) by G. L. Kedderis, et al., "Studies With Nitrogen–Containing Steroids . . .".

Bioinorganic Chemistry, 17, pp. 372–376 (1986) by B. W. Metcalf, et al., "Patent Inhibition of Human Steroid . . . by 3–Androstene–3–Carboxylic Acid".

Biochemistry, 1990, vol. 29, pp. 2815–2824, by M. A. Levy, et al., "Inhibition of Rat Liver Steroid 5 Alpha–Reductase . . . ".

J. Med. Chem., 1990, vol. 33, pp. 943–950, by D. A. Holt, et al. "Steroidal A Ring Carboxylic Acids . . . ".

J. Steroid Biochem., vol. 34, Nos. 1–6, pp. 571–575 (1989), by M. A. Levy, et al., "Interaction Between Rat Prostatic 5 Alpha–Reductase . . . ".

J. Med. Chem., vol. 33, pp. 937–942 (1990) by D. A. Holt, et al., "Steroidal A Ring Aryl Carboxylic Acids".

TIPS, Dec. 1989, vol. 10, pp. 491–495, by D. W. Metcalf, et al., "Inhibitors of . . . 5 Alpha–Reductase in Benign Prostatic Hyperplasia . . . ".

Steroids, vol. 35, No. 3 (Mar. 1980) pp. 1–7, by L. Murphy, et al., "Effect of Estradiol on a . . . Binding Protein in the Uterus of the Mouse".

Prostate, vol. 9, pp. 311–318 (1986) by N. Stone, et al., "Estrogen Formation in Human Prostatic Tissue . . . ".

Steroids, vol. 47, No. 1, pp. 1–19 (1986) by J. R. Brooks, et al., "5 Alpha–Reductase Inhibitiory . . . Activities of Some 4–Azasteroids . . .".

Lancet, No. 1986, No. 8515, pp. 1095–1096, by F. Labrie, et al. "Combination therapy in prostate cancer".

J. Clin. Endocrin. and Metab., vol. 55, No. 1, pp. 188–193 (1987), by R. Rittmaster, et al., "The Effects of . . . a 5 Alpha–Reductase Inhibitor . . . ".

J. Clin. Endocrin and Metab., vol. 74, No. 2, pp. 345–350 (1990), by A. Diani, et al., "Hair Growth Effects of Oral Administration of Finasteride . . . ".

J. Clin. Endocrinol. Metab. 67, No. 4, pp. 808–816 (1988), by N. Bruchovsky, et al., "Kinetic Parameters of 5 Alpha–Reductase Activity in Stroma & Epithelium of Normal, Hyperplastic, & Carcinomatous Human Prostates".

J. Steroid Biochem. 26, (3) pp. 349–353 (1987), by R. Hudson, "Comparison of Nuclear 5 Alpha–Reductase Activities in the Stromal and Epithelial Fractions of Human Prostatic Tissue".

J. Biol. Chem. 251, (19) pp. 5895–5900 (1976), by R. J. Moore, et al., "Steroid 5 Alpha–Reductase in Cultured Human Fibroblasts".

J. Biol. Chem. 264, (27) pp. 16249–16255 (1989), by S. Andersson, et al., "Expression Cloning & Regulation of steroid 5 alpha–Reductase, an Exzyme Essential for Male Sexual Differentiation".

Proc. Nat'l Acad. Science 87, pp. 3640–3644 (1990), by S. Andersson, et al., "Structural & Biochemical Properties of cloned and expressed human and rat steroid 5 alpha–reductases".

Nature 354, pp. 159–161 (Nov. 14, 1991), by S. Andersson, et al., "Deletion of Steroid 5 Alpha–Reductase–2 Gene in Male Pseudohermaphroditism".

Biol. of Reproduction, vol. 46, pp. 168–173 (1992), by J. D. Wilson, "Syndromes of Androgen Resistance".

Eur. J. Cancer 26 (2), p. 188 (1990), by A. A. Geldof, et al., "Enzyme Inhibitors in Hormone Dependent Prostate Cancer Growth".

J. Cancer Res. Clin. Oncol. 118, pp. 50–55 (1992), by A. Geldof, et al., "Consideration of the Use of . . . 4MA . . . in Prostate Cancer Therapy".

The Prostate 18, pp. 215–227 (1991), by J. Brooks, et al., "Effect of Castration, DES, Flutamide, and MK–906 on Growth of the Dunning Rat Prostatic Carcinoma . . . ".

Eur. J. Pharm. 183 (5), p. 1757 (1990), by Y. Masubuchi, et al., "Lack of DHT Inhibition . . . by Treatment of 4MA . . . ".

Kedderis et al. "Studies with Nitrogen–Containing Steroids and Freshly Isolated Rat Hepatocytes, Role of Cytochrome p–450 in Detoxification" Toxicology & Appl. Pharmacol. 93: 403–412 (1988).

Burger, Medicinal Chem. 2nd Ed. Interscience NY p. 42 (1960).

Back et al., "N. Chloroazasteroids: A Novel Class of Reactive Steroid Analogues, Preparation Reactioin with Thiols and Photochemical Conversion to Electrophilic N–Acyl Imines" J. Org. Chem. 54: 1904–10 (1989).

Helliker, "Alopecia Suffers Seek to Suffer Less and not in Silence", Wall Street Journal, Jun. 7, 1992 pp. A1, A7.

"Stinson, Prostate, Drug Proscar Cleared for Marketing", Chemical & Eng. News, Jun. 29, 1992, pp. 7–8.

Derwent Drug File Abstract, Ringdoc Profile 47, Accession No. 9, 90–28432 (1990).

17-ETHERS AND THIOETHERS OF 4-AZA-STEROIDS

This is a section 371 filing of PCT/US 93104746 filed May 19, 1993 which is a continuation in part of application Ser. No. 07/886031, filed May 20, 1992, now abandoned.

BACKGROUND OF THE INVENTION

The present invention is directed to new 17-position ether and thioether derivatives of 4-aza-androstan-3-ones and related compounds, and the use of such compounds as 5α-reductase inhibitors.

The art reveals that certain undesirable physiological manifestations, such as acne vulgaris, seborrhea, female hirsutism, male pattern baldness and benign prostatic hypertrophy, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It is now known in the art that the principal mediator of androgenic activity in some target organs is 5α-dihydrotestosterone, and that it is formed locally in the target organ by the action of testosterone-5α-reductase. It is also known that inhibitors of testosterone-5α-reductase will serve to prevent or lessen symptoms of hyperandrogenic stimulation.

A number of 4-aza steroid compounds are known in the art as 5α-reductase inhibitors. For example, See U.S. Pat. Nos. 2,227,876, 3,239,417, 3,264,301 and 3,285,918; French Patent No. 1,465,544; Doorenbos and Solomons, J. Pharm. Sci. 62, 4, pp. 638–640 (1973); Doorenbos and Brown, J. Pharm. Sci., 60, 8, pp. 1234–1235 (1971); and Doorenbos and Kim, J. Pharm. Sci. 63, 4, pp. 620–622 (1974).

In addition, U.S. Pat. Nos. 4,377,584, 4,220,775, 4,859, 681, 4,760,071 and the articles J. Med. Chem. 27, p. 1690–1701 (1984) and J. Med. Chem. 29, 2998–2315 (1986) of Rasmusson, et al., U.S. Pat. No. 4,845,104 to Carlin, et al., and U.S. Pat. No. 4,732,897 to Cainelli, et al. describe 4-aza-17β-substituted-5α-androstan-3-ones which are said to be useful in the treatment of DHT-related hyperandrogenic conditions.

However, despite the suggestion in the prior art that hyperandrogenic diseases are the result of a single 5α-reductase, there are reports regarding the presence of other 5α-reductase isozymes in both rats and humans. For example, in human prostate, Bruchovsky, et al. (See J. Clin. Endocrinol. Metab. 67, 806–816, 1988) and Hudson (see J. Steroid Biochem. 26, p 349–353, 1987) found different 5α-reductase activities in the stromal and epithelial fractions. Additionally, Moore and Wilson described two distinct human reductases with peaks of activities at either pH 5.5 or pH 7–9. (See J. Biol. Chem. 251, 19, p. 5895–5900, 1976.)

Recently, Andersson and Russell isolated a cDNA which encodes a rat liver 5α-reductase (see J. Biol. Chem. 264 pp. 16249–55 (1989). They found a single mRNA which encodes both the liver and prostatic reductases of rats. The sequence of this rat gene was later used to select a human prostatic cDNA encoding a 5α-reductase termed "5α-reductase 1". (See Proc. Nat'l. Acad. Sci. 87, p. 3640–3644, 1990.)

More recently, a second, human prostatic reductase (5α-reductase 2) has been cloned with properties identified with the more abundant form found in crude human prostatic extracts. (See Nature, 354, p. 159–161, 1991.)

Further, "Syndromes of Androgen Resistance"—The Biology of Reproduction, Vol. 46, p. 168–173 (1992) by Jean O. Wilson indicates that the 5α-reductase 1 enzyme may be associated with hair follicles.

Thus, the art supports the existence of at least two genes for 5α-reductase and two distinct isozymes of 50α-reductase in humans. Both forms are present in prostatic tissue in which, 5α-reductase 2, is the more abundant, and the other isozyme, 5α-reductase 1, is believed to be more abundant in scalp tissue.

In the treatment of hyperandrogenic disease conditions, e.g. benign prostatic hyperplasia (BPH), it would be desirable to have one drug entity which is active against both enzymes 1 and 2 in the prostate to substantially inhibit dihydrotestosterone (DHT) production. Alternatively, it would be desirable to have a drug entity which is highly selective for inhibiting the scalp associated enzyme 50α-reductase 1, for use in treating diseases of the skin and scalp, e.g. acne and alopecia. The drug could also be used in combination with PROSCAR® (finasteride) which is highly selective for the prostatic enzyme 5α-reductase 2 for combination therapy in the treatment of BPH.

SUMMARY OF THE INVENTION

The present invention discloses novel 17-position ether and thioether derivatives of 4-aza-androstan-3-ones and related compounds which are useful for inhibiting the steroid 5α-reductase enzymes 1 and 2. The compounds are particularly effective in selectively inhibiting the 5α-reductase 1 associated with the scalp, and dually inhibiting both isozymes 1 and 2 in the oral, parenteral or topical treatment of benign prostatic hyperplasia, acne, female hirsutism, male pattern baldness, androgenic alopecia, prostatitis, and the treatment of prostatic carcinoma.

DETAILED DESCRIPTION OF THE INVENTION

This invention is concerned with compounds of formula I, and combinations thereof for the selective inhibition of 5α-reductase 1 and the combined inhibition of 5α-reductase 1 and 2. Compounds of formula I are defined as follows:

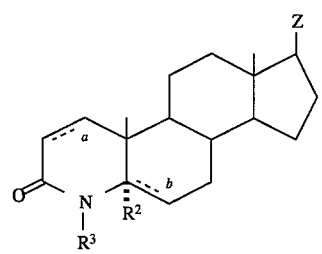

wherein a and b are both single bonds and $R^2$ is hydrogen, or a is a double bond, b is a single bond and $R^2$ is hydrogen, or a is a single bond, b is a double bond and $R^2$ is absent;

Z is —$XR^4$, or —$(CHR^1)_n$-$XR^4$;

n is an integer selected from 1–10;

X is —O— or —$S(O)_p$—, wherein p is zero, 1 or 2;

$R^1$ is —H, aryl, or —$C_{1-3}$alkyl unsubstituted or substituted with aryl and when n is greater than 1, $R^1$ can be the same or different at each ocurrence;

$R^3$ is —H, methyl, ethyl, —OH, —$NH_2$ or —$SCH_3$;

$R^4$ is 1) —$C_{1-20}$ alkyl, unsubstituted or substituted with one or more of:
 a) —OH,
 b) halo,
 c) —$C_{1-8}$ alkoxy,
 d) —$C_{1-10}$ alkenyl,
 e) —$CONR^5R^5$, wherein $R^5$ is independently
  i) —H,
  ii) —$C_{1-8}$ alkyl unsubstituted or substituted with one or more of $R^7$, aryl or heterocycle, the aryl being unsubstituted or substituted with one or more of $R^7$ or $R^9$,
  iii) aryl unsubstituted or substituted with one or more of $R^7$ or $R^9$, or
  iv) heterocycle, unsubstituted or substituted with one or more of $R^7$ or $R^9$,
 f) —$COOR^6$, wherein $R^6$ is
  i) —H,
  ii) —$C_{1-8}$ alkyl unsubstituted or substituted with one or more of $R^7$ or aryl, the aryl being unsubstituted or substituted with one or more of $R^7$ or $R^9$, or
  iii) aryl, unsubstituted or substituted with one or more of $R^7$ or $R^9$,
 g) —$S(O)_p$—$R^5$, wherein p is defined above,
 h) —$N(R^5)_2$,
 i) aryl, unsubstituted or substituted with one or more of aryl, $R^7$ or $R^9$,
 j) heterocycle, unsubstituted or substituted with one or more of $R^7$ or $R^9$,
 k) —$C_{3-10}$ cycloalkyl, such as cyclohexyl, norbomyl, or adamantyl, unsubstituted or substituted with one or more of $R^7$ or $R^9$, or
 l) —$CONR^8$—CO-$NHR^8$, wherein $R^8$ is —H, —$C_{1-8}$ alkyl, benzyl or cyclohexyl, 2) aryl, unsubstituted or substituted with one or more of aryl, $R^7$ or $R^9$, or 3) heterocycle or —$C_{3-10}$ cycloalkyl, either of which is unsubstituted or substituted with one or more of $R^7$ or $R^9$;

$R^7$ is
 1) —OH,
 2) —$C_{1-3}$ alkoxy,
 3) —CN,
 4) 1'$COOR^6$
 5) —$C_{1-8}$alkyl —$COOR^6$
 6) —$NO_2$, or
 7) —halo; and
 8) amino, mono —$C_1$-$C_4$ alkylamino, di-$C_1$-$C_4$-alkylamino;

$R^9$ is
 1) —$C_{1-8}$ alkyl, unsubstituted or substituted with one or more of aryl or $R^7$,
 2) —CO-A, —$C_{1-8}$ alkyl-CO-A, —NHCO-A, or —$S(O)_p$-A, wherein p is defined above and A is
  a) —H, b) —$C_{1-8}$ alkyl, unsubstituted or substituted with one or more of
  i) —$R^7$, or
  ii) aryl, unsubstituted or substituted with one or more of $R^7$, or
 c) aryl, unsubstituted or substituted with one or more of $R^7$, 3) —NHCO-heterocycle, 4) —$N(R^{10})_2$ or —$CON(R^{10})_2$ wherein $R^{10}$ is independently heterocycle, or —A, 5) —NHCO-$(CH_2)_q$-CO-Q, wherein q is 1–4, and Q is —$N(R^{10})_2$ or —$OR^{10}$; with the proviso that when Z is —$OR^4$, $R^3$ is —H, a is a single bond and b is a single or double bond, $R^4$ is not isopentyl; or a pharmaceutically acceptable salt or ester thereof.

A first preferred embodiment of this invention is represented by compounds of formula II

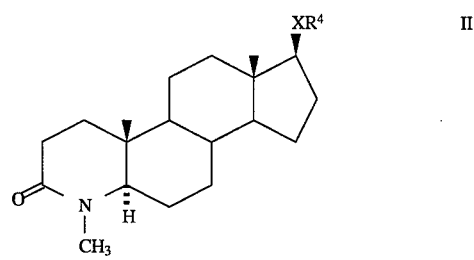

wherein $R^4$ is —$C_{1-20}$ alkyl, unsubstituted or substituted with one or more of
 —OH, halo, —$C_{1-8}$alkoxy, —$C_{1-6}$alkenyl, —$S(O)_p$-$R^5$, —$N(R^5)_2$, aryl unsubstituted or substituted with one or more of aryl, $R^7$ or $R^9$, heterocycle unsubstituted or substituted with one or more of $R^7$ or $R^9$, or —$C_{3-10}$ cycloalkyl unsubstituted or substituted with one or more of $R^7$ or $R^9$ and X, p, $R^5$, $R^7$ and $R^9$ are all defined as in formula I.

A second preferred embodiment of this invention is represented by compounds of formula II wherein $R^4$ is —$C_{1-20}$ alkyl substituted with —$CONR^5R^5$, —$COOR^6$ or —$CONR^8CONHR^8$, and X, $R^5$, $R^6$ and $R^8$ are defined as in formula I.

A third preferred embodiment of this invention is represented by compounds of formula II wherein $R^4$ is aryl unsubstituted or substituted with one or more of aryl, $R^7$ or $R^9$;

heterocycle unsubstituted or substituted with one or more of $R^7$ or $R^9$; or

—$C_{3-10}$ cycloalkyl unsubstituted or substituted with one or more of $R^7$ or $R^9$; and X, $R^7$ and $R^9$ are defined as in formula I.

A fourth preferred embodiment of this invention is represented by compounds of formula III

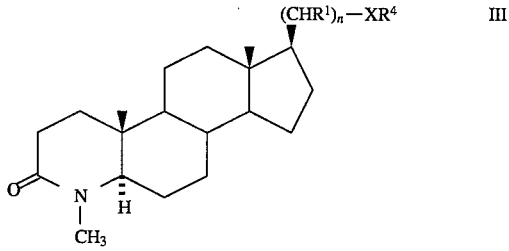

wherein $R^4$ is —$C_{1-20}$ alkyl, unsubstituted or substituted with one or more of
 —OH, halo, —$C_{1-8}$alkoxy, —$C_{1-6}$alkenyl, —$S(O)_p$-$R^5$, —$N(R^5)_2$, aryl unsubstituted or substituted with one or more of aryl, $R^7$ or $R^9$, heterocycle unsubstituted or substituted with one or more of $R^7$ or $R^9$, or —$C_{3-10}$ cycloalkyl unsubstituted or substituted with one or more of $R^7$ or $R^9$, and X, $R^1$, n, p, $R^5$, $R^7$ and $R^9$ are defined as in formula I.

A fifth preferred embodiment of this invention is represented by compounds of formula III wherein $R^4$ is —$C_{1-20}$ alkyl substituted with —$CONR^5R^5$, —$COOR^6$ or —$CONR^8CONHR^8$, and X, $R^1$, n, $R^5$, $R^6$ and $R^8$ are defined as in formula I.

A sixth preferred embodiment of this invention is represented by compounds of formula III wherein $R^4$ is aryl unsubstituted or substituted with one or more of aryl, $R^7$ or $R^9$;

heterocycle unsubstituted or substituted with one or more of $R^7$ or $R^9$; or

—$C_{3-10}$ cycloalkyl unsubstituted or substituted with one or more of $R^7$ or $R^9$; and X, $R^1$, n, $R^7$ and $R^9$ are defined as in formula I.

Unless stated otherwise, the 17-position substituent is assumed to be in the beta configuration.

Novel compounds of the present invention include but are not limited to the following compounds:

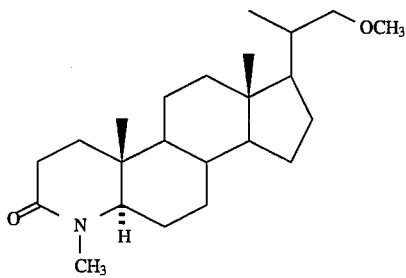

20-(methoxymethyl)-4-methyl-5α-4-azapregnan-3-one,

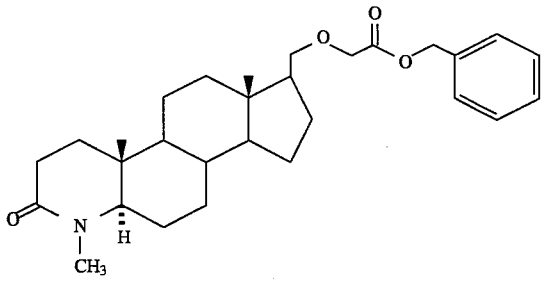

17-(carbobenzyloxymethoxymethyl)4-methyl-5α-4-azaandrostan- 3-one,

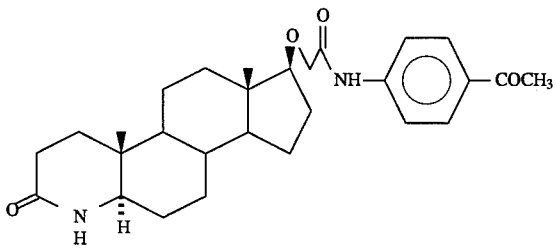

5α-4-azaandrostan-3-on-17β-yloxy-N-(4-acetylphenyl)acetamide,

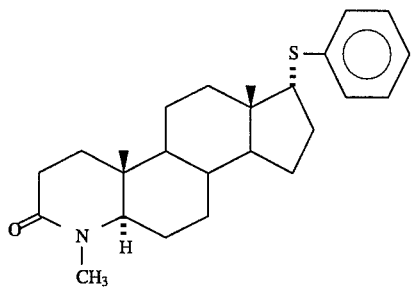

17α-thiophenoxy-4-methyl-5α-4-azaandrostan-3-one,
17-(methoxymethyl)-4-methyl-5α-4-azaandrostan-3-one,
17-(ethylthiomethyl)-4-methyl-5α-4-azaandrostan-3-one,
17-(carboxymethoxymethyl)-4-methyl-5α-4-azaandrostan-3-one,
17-(carboethoxymethoxymethyl)-4-methyl-5α-4-azaandrostan-3-one,
17-(carbobenzyloxymethoxymethyl)4-methyl-5α-4-azaandrostan-3-one,
17-(diphenylmethoxymethyl)-4-methyl-5α-4-azaandrostan-3-one,
20-(diphenylmethoxy)-4-methyl-5α-4-azapregnan-3-one,
20-methoxy-4-methyl-5α-4-azapregnan-3-one,
20-(methoxymethyl)-4-methyl-5α-4-azapregnan-3-one,
20-(diphenyimethoxymethyl)-4-methyl-5α-4-azapregnan-3-one,
20-(ethylthiomethyl)-4-methyl-5α-4-azapregnan-3-one,
20-(isopropylthiomethyl)-4-methyl-5α-4-azapregnan-3-one,
ethyl-4-methyl-5α-4-azaandrostan-3-on-17β-yloxyacetate,
diphenylmethyl 4-methyl-5α-4-azaandrostan-3-on-17β-yloxyacetate,
4-methyl-5α-4-azaandrostan-3-on- 17β-yloxy-N-(3,4-dichlorobenzyl)acetamide,
4-methyl-5α-4-azaandrostan-3-on-17β-yloxy-N-phenylacetamide,
4-methyl-5α-4-azaandrostan-3-on-17β-yloxyacetic acid,
4-methyl-5α-4-azaandrostan-3-on-17β-yloxy-N-( 4-acetylphenyl)acetamide,
4-methyl-5α-4-azaandrostan-3-on-17β-yloxyacetamide,
7β-(4-biphenyloxy)-4-methyl-5α-4-azaandrostan-3-one,
7β-(2,4-dinitrophenoxy)-4-methyl-5α-4-azaandrostan-3-one,
4-methyl-17α-phenoxy-5α-4-azaandrostan-3-one,
17α-(4-biphenyloxy)-4-methyl-5α-4-azaandrostan-3-one,
17β-diphenylmethoxy-4-methyl-5α-4-azaandrostan-3-one,
4-methyl-17α-thiophenoxy-5α-4-azaandrostan-3-one,
4-methyl-17α-phenylsulfonyl-5α-4-azaandrostan-3-one,
4-methyl-17α-phenylsulfinyl-5α-4-azaandrostan-3-one (isomer a),
4-methyl-17α-phenylsulfinyl-5α-4-azaandrostan-3-one (isomer b),
4-methyl-17β-(4-nitrophenoxy)-5α-4-azaandrostan-3-one,
17β-(4-aminophenoxy)-4-methyl-5α-4-azaandrostan-3-one hydrochloride,
17β-(4-acetamidophenoxy)-4-methyl-5α-4-azaandrostan-3-one,
17β-(4-cyanophenoxy)-4-methyl-5α-4-azaandrostan-3-one,
17β-(4-carboxamidophenoxy)4-methyl-5α-4-azaandrostan-3-one,
17β-methyleneoxy-[N-cyclohexyl-N-(N-cyclohexyl-carbamoyl)carbamoyl]4-methyl-5α-4-azaandrostan-3-one,
4-methyl-17β-(3-pyridyl)oxy-5α-4-azaandrostan-3-one, 4-methyl-17β-(2-pyridyl)methoxy-5α-4-azaandrostan-3-one,
17β-benzyloxy-4-methyl-5α-4-azaandrostan-3-one,
ethyl 5α-4-azaandrostan-3-on-17β-yloxyacetate,
5α-4-azaandrostan-3-on-17β-yloxyacetic acid,
5α-4-azaandrostan-3-on-17β-yloxy-N-phenylacetamide,
5α-4-azaandrostan-3-on-17β-yloxy-N-(4-acetylphenyl)acetamide,
diphenylmethyl 5α-4-azaandrostan-3-on-17β-yloxyacetate,
17β-methyleneoxy-[N-cyclohexyl-N-(N-cyclohexyl-carbamoyl)carbamoyl]- 5α-4-azaandrostan-3-one,
5α-4-azaandrostan-3-on-17β-yloxy-N-[4-( 1(RS)-hydroxyethyl)-phenyl]acetamide,
5α-4-azaandrostan-3-on- 17β-yloxy-N-(4-t-butylphenyl)acetamide,
17β-methyleneoxy-[N-isopropyl-N-(N-isopropylcarbamoyl)-carbamoyl]- 5α-4-azaandrostan-3-one,
17-(4-methylpentyloxy)4-methyl-5α-4-azaandrostan-3-one,
17-hexyloxy-4-methyl-5α-4-azaandrostan-3-one,
4-methyl-17-propyloxy-5α-4-azaandrostan-3-one,
4-methyl-17-undecyloxy-5α-4-azaandrostan-3-one,
17-allyloxy-4-methyl-5α-4-azaandrostan-3-one,
17-allyloxy-4-methyl-4-azaandrost-5-en-3-one, and
17-hexyloxy-4-methyl-4-azaandrost-5-en-3-one.

Novel compounds of this invention further include, but are not limited to:
17-(4-(isobutyl)benzyloxy)methyl-4-methyl-5α-4-azaandrostan-3-one,
17-(4-acetamidobenzyloxy)methyl-4-methyl-5α-4-azaandrostan-3-one,
4-methyl-17-(3-nitrobenzyloxy)methyl-5α-4-azaandrostan-3-one,
4-methyl-17-(phenoxyethoxymethyl)-5α-4-azaandrostan-3-one,
17-(3 -(isopropylthio)propyloxy)methyl-4-methyl-5α-4-azaandrostan-3-one,
17-(2-fluorobenzyloxy)methyl-4-methyl-5α-4-azaandrostan-3-one,
4-methyl-17-(3-(trifluoromethyl)benzyloxy)methyl- 5α-4-azaandrostan-3-one,
17-(4-dimethylaminobenzyloxy)methyl-4-methyl- 5α-4-azaandrostan-3-one,
17-((N-t-butyl-carboxamido)methoxymethyl)-4-methyl-5α-4-azaandrostan-3-one,
20-(3-(ethylthio)propyl)-4-methyl-5α-4-azapregnan-3-one,
20-(2-(benzyloxy)ethyl)-4-methyl-5α-4-azapregnan-3-one,
20-(3-methoxybenzyloxy)methyl-4-methyl-5α-4-azapregnan-3-one,
17α-(carboethoxymethoxy)benzyl-4-methyl-5α-4-azaandrostan-3-one,
20-(4-(methylthio)benzyloxy)methyl-4-methyl-5α-4-azapregnan-3-one,
4-methyl-17-n-octylthiomethyl-5α-4-azaandrostan-3-one,
20-(t-butylthiomethyl)-4-methyl-5α-4-azapregnan-3-one,
17-(2-furfuryl)thiomethyl-4-methyl-5α-4-azaandrostan-3-one,
17-(geranyloxymethyl)-4-methyl-5α-4-azaandrostan-3-one,
4-methyl-20-(2-(n-nonylthio)ethyl)-5α-4-azapregnan-3-one,
20-(methylthiomethyl)-4-methyl-5α-4-azapregnan-3-one,
17-(4-(benzyloxy)benzyloxy)methyl-4-methyl- 5α-4-azaandrostan-3-one,
20-(diphenylmethylthio)methyl-4-methyl-5α-4-azapregnan-3-one,
17-(3-(ethylthio)propyl)-4-methyl-5α-4-azaandrostan-3-one,
4-methyl-20-(phenylthiomethyl)-5α-4-azapregnan-3-one,
17-(ethylsulfonylmethyl)-4-methyl-5α-4-azaandrostan-3-one, or
17-(4-ethoxybenzyloxy)methyl-4-methyl-5α-4-azaandrostan-3-one.

Also included within the scope of this invention are pharmaceutically acceptable salts or esters, where a basic or acidic group is present in a compound of formula I, such as on the substituted alkyl, cycloalkyl, aryl or heterocyclic moiety. When an acidic substituent is present, i.e. —COOH, there can be formed the ammonium, sodium, potassium, calcium salt, and the like, for use as the dosage form.

Where a basic group is present, i.e. amino, acidic salts, i.e. hydrochloride, hydrobromide, acetate, pamoate, and the like, can be used as the dosage form.

Also, in the case of the —COOH group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

The compounds of the present invention, may have asymmetric centers and occur as racemates, racemic mixtures and as individual diastereomers, with all isomeric forms being included in the present invention.

When any variable (e.g., aryl, heterocycle, $R^1$, $R^2$, n, X, etc.) occurs more than one time in any constituent or in formula I, II or III, its definition on each occurrence is independent of its definition at every other occurrence. Also, combinations of substituents and/or variables are permissible only if such combinations result in stable compounds.

As used herein "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge. "Cycloalkyl" is intended to include saturated mono-, bi- and tricyclic ring groups, such as cyclopropyl, cyclobutyl, cyclopentyl, cyclohexyl (Cyh), cycloheptyl, norbomanyl and adamantyl. "Alkenyl" is intended to include hydrocarbon groups of either a straight or branched configuration with one or more carbon-carbon double bonds which may occur in any stable point along the chain, such as ethenyl, propenyl, butenyl, pentenyl, and the like. "Halo", as used herein, means fluoro, chloro, bromo and iodo.

As used herein, with exceptions as noted, "aryl" is intended to mean phenyl (Ph) or naphthyl.

The term heterocycle or heterocyclic, as used herein except where noted, represents a stable 5- to 7-membered monocyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl. Preferred heterocycles are piperidinyl, 2-oxopyrrolodinyl, pyrrolyl, pyrazolyl, imidazolyl, pyridyl, pyrazinyl, pyrimidinyl, pyridazinyl, oxazolyl, isoxazolyl, morpholinyl, thiazolyl, isothiazolyl, quinuclidinyl, indolyl, quinolinyl, isoquinolinyl, benzimidazolyl, thiadiazoyl, benzothiazolyl, benzoxazolyl, furyl, tetrahydrofuryl, thienyl, and benzothienyl.

As used herein, "heteroaryl" represents a stable 5- to 7-membered monocyclic unsaturated heterocyclic ring, which consists of carbon atoms and from one to three heteroatoms selected from the group consisting of N, O and S, and wherein the nitrogen and sulfur heteroatoms may optionally be oxidized, and the nitrogen heteroatom may optionally be quaternized.

Further abbreviations that may appear herein are defined as follows:

| | |
|---|---|
| DCC | N,N'-dicyclohexylcarbodiimide |
| DIC | 1,3-diisopropylcarbodiimide |
| DEAD | diethyl azodicarboxylate |
| DMAP | 4-dimethylaminopyridine |
| DMF | N,N-dimethylformamide |
| DMSO | dimethyl sulfoxide |
| EtOAc | ethyl acetate |
| Ph$_3$P | triphenylphosphine |
| m.p (or mp) | melting point |
| THF | tetrahydrofuran |
| m.w. (or mw) | molecular weight |

The compounds of the present invention are made by methods known to those skilled in the art, and are described as follows and in schemes 1–4.

The compounds of this invention are generally made from asteroid alcohol starting material, represented by formula (i)

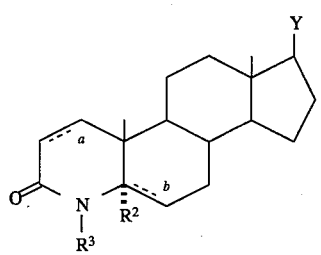

wherein a and b are both single bonds and $R^2$ is hydrogen, or a is a double bond, b is a single bond and $R^2$ is hydrogen, or a is a single bond, b is a double bond and $R^2$ is absent; $R^3$ is —H, methyl or ethyl; Y is —OH or —(CHR$^1$)$_n$—OH; $R^1$ is —H, aryl, or C$_{1-3}$ alkyl unsubstituted or substituted with aryl; and n is 1–10. Methods of making starting alcohols of formula (i) are well know to those skilled in the art, and are described, for example, in the following publications: Rasmusson, G. H., et al., *J. Med. Chem.*, 29, 2298–2315 (1986); Rasmusson, G. H., et al., *J. Med. Chem.*, 27 1690–1701 (1984).

Furthermore, the starting 4-azasteroid-20-alcohols of formula (i) may be made by several methods well known to those skilled in the art. For example, 4-azasteroids containing a 17-carbonyl group (e.g. carboxaldehyde) may be reacted with the appropriate organo-metallic reagent to yield the corresponding secondary alcohol, while reduction yields the primary alcohol. Also, an appropriate 17-ketone may be reduced (e.g. with sodium borohydride) to the desired alcohol. The above mentioned ketones may be made by several methods well known in the art; one particularly useful method is that of A. Bhattacharya et al., Synthetic Communications 20 (17), 2683–2690 (1090), in which an activated carbonyl compound is reacted with a suitable Grignard reagent to give the desired ketone. Other activated carbonyl compounds (e.g. pyridine thioesters) may also be used. These alcohol functions may be constructed both before and after the formation of the 4-aza moiety.

For purposes of illustration, schemes 1–4 below employ specific steroid alcohol starting materials such as 17-hydroxymethyl-4-methyl- 5α-4-azaandrostan-3-one (compound (ii) below) or 17-hydroxy- 4-methyl-5α-4-azaandrostan-3-one (compound (v) below) as the starting alcohol. However, the present invention and the synthetic methods described herein are not limited by the use of any particular compounds in any of the schemes or synthetic descriptions presented below, except where otherwise noted, but rather the schemes and synthetic descriptions are presented for illustrative purposes to those skilled in the art. A person skilled in the art would be able to choose the appropriate alcohol starting material to use in the following general synthetic route descriptions to arrive at a target product within the scope of genetic formula I.

As depicted in Scheme I below, thioethers (iv) can generally be made by forming the mesylate (iii) of alcohol (ii) by common methods known in the art, e.g. using methanesulfonyl chloride in CH$_2$Cl$_2$ with pyridine, and then treating the mesylate with M$^+$S$^-$-R$^4$, wherein M$^+$ is a metal ion, e.g. Na$^+$ or K$^+$, and R$^4$ is as defined in formula I. The M$^+$S$^-$-R$^4$ reagents are either commercially available, such as sodium thioethoxide or potassium thiophenoxide, or can be generated by methods well known in the art, e.g., as described in *J.Org. Chem*, 40, p 1181 (1975) or *J. Chem. Soc.*, p 3127 (1928).

SCHEME 1

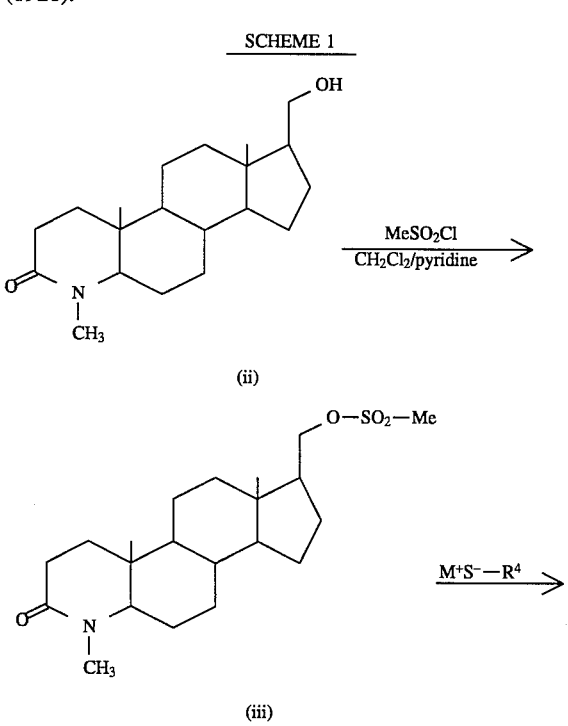

-continued
SCHEME 1

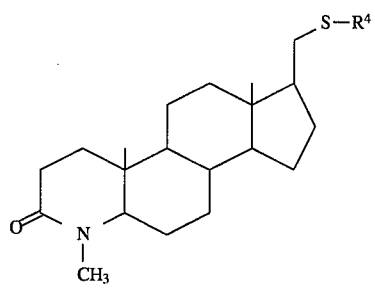

(iv)

As depicted in Scheme 2, below, the starting alcohol (v) can be treated with a diazo-reagent (vi) using techniques well known in the art, e.g. using boron trifluoride etherate or $Rh_2(OAc)_4$, to obtain ethers of formula (vii). Diazo-reagents, such as diazomethane, diphenyl-diazomethane, benzyl diazoacetate, etc., are generated by methods well know in the art, such as by the methods described in the following publications: British Patent 1,533,381; British Patent 1,459,285; *J. Chem. Soc.*, Perkins I, p. 2030 (1975); *Organic Synthesis*, Collective. Vol. III, p. 351 (1955); *J. Org. Chem.*, 24, p. 560 (1959).

When $R^a$ is —H and $R^b$ is —$COOC_2H_5$ in compound (vii), hydrolysis of the ester with base followed by treatment with acid produces compound (viii). The acid (viii) can be coupled with an amine, e.g. an arylamine such as aniline, 4-t-butyl aniline, or p-amino-acetophenone, by common amide coupling procedures well known in the art, e.g., using the carbodiimide method with reagents such as DCC or DIC in the presence of DMAP, to form an amide exemplified by (x). When DCC is used, the sideproduct (xi) can be formed as well; when DIC is used, a sideproduct similar to (xi) can be formed except instead of a cyclohexyl urea moiety, it contains an isopropyl urea moiety. Treatment of (viii) with a diazo reagent, such as diphenyl diazomethane, and $Rh_2(Ac)_4$ under conditions well known in the art leads to formation of compounds exemplified by (ix).

The 5α-4-azandrostan-3-on-17-yloxyacetic acid and ethyl 5α-4-azaandrostan-3-on-17β-yloxy-acetate analogs can be prepared according to general scheme 2 but are more preferably prepared according to the routes described in Examples 17 and 21 herein.

SCHEME 2

(v)  →  (vii)

$R^a = R^b = $ —H;
$R^a = R^b = $ —Ph; or
$R^a = $ H and $R^b = $ —$COOC_2H_5$ or $COOCH_2Ph$.

SCHEME 2 -continued

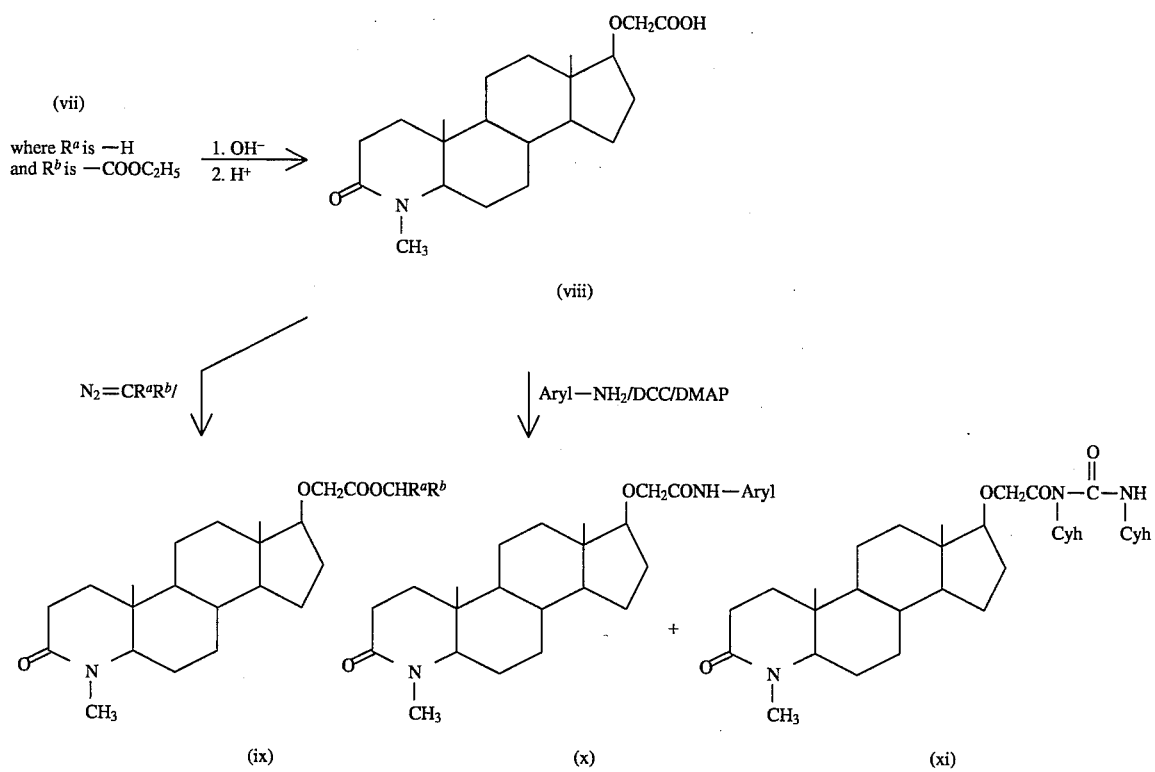

Amide compounds of formula (x) can also be made by alternative methods well known in the art, e.g., by reacting (vii) wherein $R^a$ is —H and $R^b$ is —COOC$_2$H$_5$ directly with an unsubstituted or substituted aryl-NH$_2$ compound (alkyl amine could likewise be used) and heating the reaction, e.g., to about 170° C.–180° C. (see Example 25). Another method, e.g., is to form a mixed anhydride of acid (viii) and react it with the desired primary amine to obtain compounds of formula (x) (see Example 26).

As depicted in Scheme 3, below, the starting alcohol (v) can be treated with a strong base, such as KH, NaH or KOH, in an appropriate solvent such as DMF or DMSO, followed by treatment with an alkyl- or alkenyl-halide (xii-a), such as hexyl iodide or allyl bromide for example, to form the corresponding alkyl- or alkenyl-ether product (xiii-a). Use of KOH in DMSO and KH in DMF are preferred.

SCHEME 3

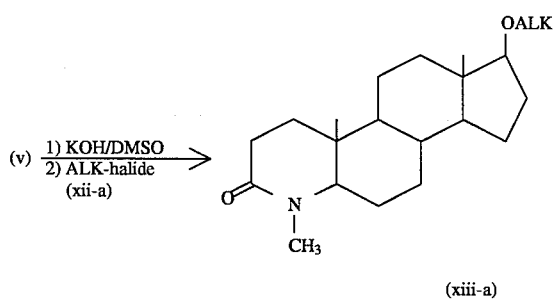

SCHEME 3 -continued

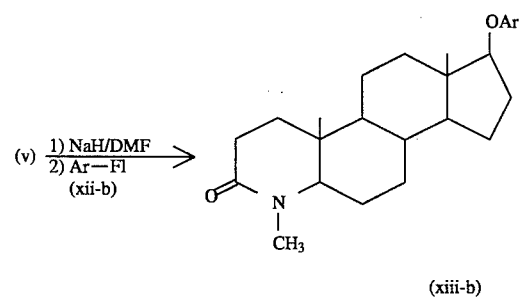

Also as depicted in Scheme 3, aryl ether and heteroaryl ether products (xiii-b) can be prepared by treating the steroid alcohol starting material with a fluoroaryl or fluoroheteroaryl compound (xii-b), such as p-nitrofluorobenzene, p-cyanofluorobenzene or 3-fluoropyridine for example, and KH, NaH or KOH in an appropriate solvent such as DMF or DMSO, with KH/DMF and KOH/DMSO being preferred.

Alternatively, aryl ether and heteroaryl ether products of formula (xiii-b) can be prepared by treating the steroid alcohol starting material with an unsubstituted or substituted hydroxy aryl or hydroxy heteroaryl compound such as phenol or 4-hydroxybiphenyl for example, and triphenylphosphine and diethyl azodicarboxylate (DEAD). With this method, the ether product will have stereochemistry at the 17-position that is the opposite of the starting alcohol when Y is —OH in formula (i). For example, using this procedure, 4-methyl-17α-phenoxy- 5α-4-azaandrostan-3-one is the product of 17β- hydroxy-4-methyl- 5α-4-azaandrostan-3-one and phenol.

Heteroaryl ether products can be reduced by methods well known in the art, e.g., by hydrogenation in an appropriate solvent such as MeOH, in the presence of a catalyst such as palladium or platinum on carbon, to obtain compounds of formula I wherein $R^4$ is a saturated heterocycle.

As depicted in Scheme 4 below, compounds of formula (xvii) can be prepared by treating the amino hydrochloride derivative (xv) with the appropriate anhydride reagent using methods well known to those skilled in the art. "$R^d$" in Scheme 4 can be heterocycle, "A" as defined in the generic description of compounds of formula I, or —$(CH_2)_q$-CO-Q, wherein the variables "q" and "Q" are as defined in the generic description of compounds of formula I. Alternatively, compounds of formula (xvii) where $R^d$ is —$(CH_2)_q$-CO-Q can be made by treating (xv) with an anhydride of formula pound (Xv) is prepared by reduction of the nitro group of compound (xiv) wherein $R^c$ is —$NO_2$, by common techniques well known in the art, e.g., hydrogenation in the presence of a catalyst such as $PtO_2$, and treatment with an acid such as HCl. Compound (xiv) wherein $R^c$ is —$NO_2$ can be prepared by methods decribed above for making aryl ethers.

Also as depicted in scheme 4, below, the cyano group of compound (xiv), wherein $R^c$ is —CN, can be hydrolyzed by methods well known in the art, e.g., by treatment with $H_2O_2$ and base such as NaOH, to provide compound (xvi). The primary amide of (xvi) can be alkylated by methods well known in the art, such as with methyl iodide, for example, to make the secondary or tertiary amide derivatives.

SCHEME 4

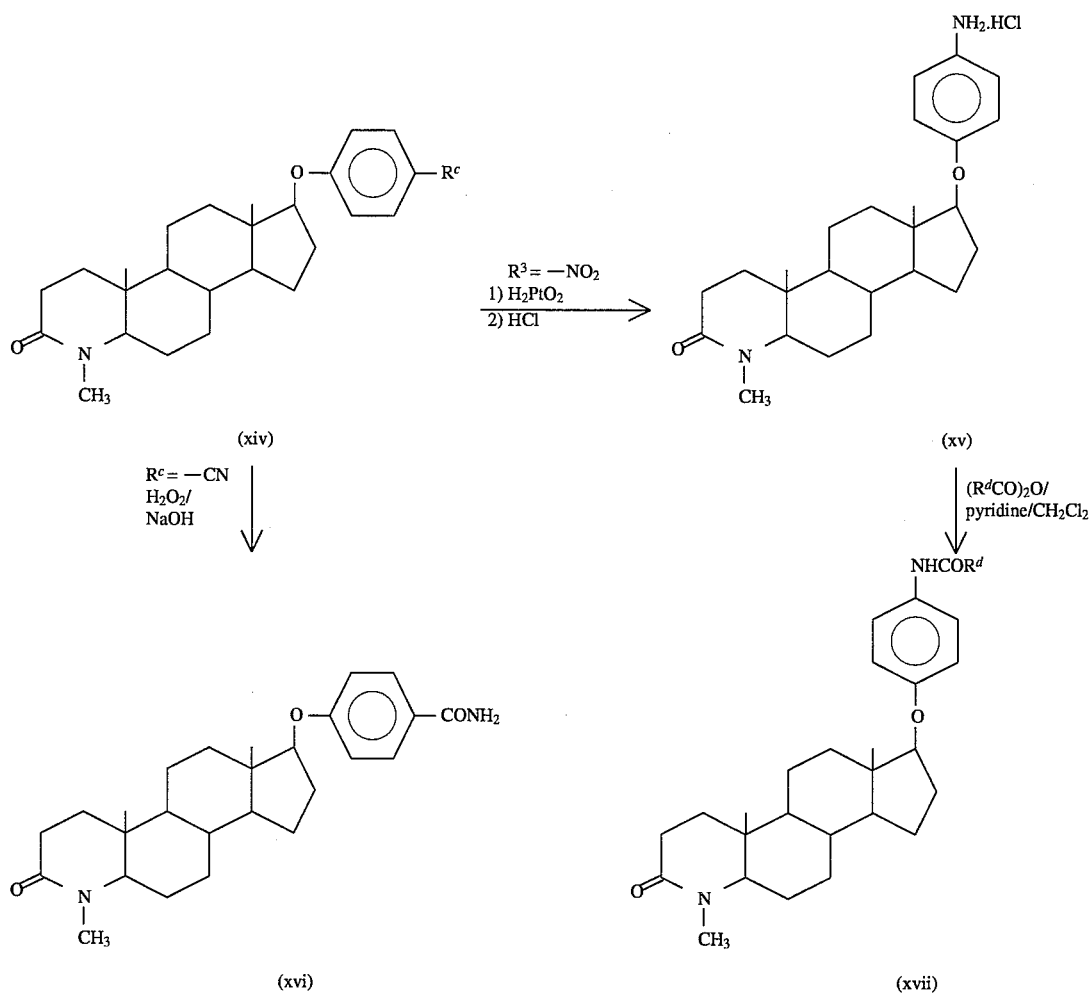

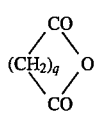

and base, such as pyridine, to make intermediate compounds of formula (xvii) where $R^d$ is —$(CH_2)_q$—COOH, and then making amides and esters from the intermediate acid. Com- By using methods well known to those skilled in the art, the diazonium salt of compound (xv) can be made by treatment of (xv) with $HNO_2$ or an alkyl nitrite. The resulting diazonium salt can be used as an intermediate in a variety of reactions to replace the diazonium moiety to make other substituted aryl ether derivatives. For example, the/ diazonium salt moiety can be replaced with a halo, —CN, —OH or alkoxy group by common methods well known to those skilled in the art. Or the diazonium moeity can be replaced with hydrogen to yield the unsubstituted aryl ether derivative.

Another preferred embodiment of this invention is a series of compounds characterized in having ether moieties at the 17 position, and which can be synthesized according to Scheme 5:

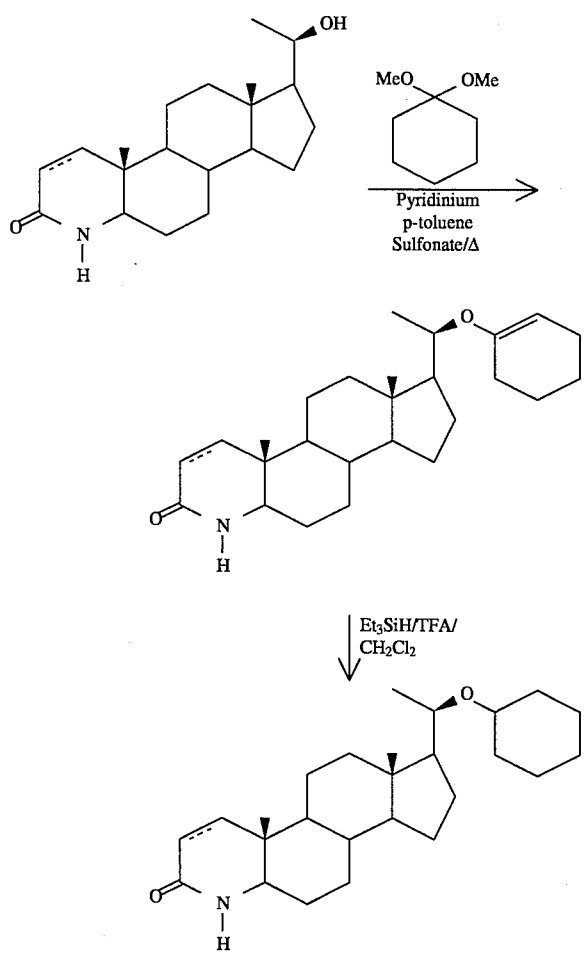

Alternatively, the ethers of this invention may be obtained by first preparing the desired ether and thioether groups at the desired position in the appropriate non-aza steroid followed by ring opening of the A-ring and subsequent closure to the desired 4-azasteroid. For example, a 20-alkoxy-substituted pregn-4-en-3-one may be oxidized with permanganate-periodate to the corresponding seco-acid which is then reacted with an appropriate amine to give, after reduction of the first obtained 4-aza-5-enesteroid, the desired 20-ether-substituted- 5α-4-azapregnan-3-one.

Accordingly, the present invention is particularly concerned with providing a method of treating the hyperandrogenic conditions of androgenic alopecia, acne vulgaris, seborrhea, and female hirsutism, benign prostatic hyperplasia, prostatitis, the treatment of prostatic carcinoma, by oral, parenteral or topical administration, of the novel compounds of the present invention.

The present invention is thus also concerned with providing suitable topical, oral and parenteral pharmaceutical formulations for use in the novel methods of treatment of the present invention.

The compositions containing the compounds of the present invention as the active ingredient for use in the treatment of e.g., benign. prostatic hypertrophy, prostatitis, and prostatic carcinoma, and hyperandrogenic conditions, can be administered in a wide variety of therapeutic dosage forms in conventional vehicles for systemic administration, as, for example, by oral administration in the form of tablets, capsules, solutions, or suspensions, of by injection. The daily dosage of the products may be varied over a wide range varying from 0.5 to 1,000 mg per adult human/per day. The compositions are preferably provided in the form of scored tablets containing 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.002 mg. to about 50 mg./kg. of body weight per day. Preferably the range is from about 0.01 mg. to 7 mg./kgs. of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calciuim phosphate, lactose, corn starch or magnesium stearate. The liquid forms in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservative are employed when intravenous administration is desired.

For the treatment of androgenic alopecia, acne vulgaris, seborrhea, female hirsutism, the compounds of the present invention are administered in a pharmaceutical composition comprising the active compound in combination with a pharmacologically acceptable carrier adapted for topical administration. Parenteral or oral administration are also applicable. These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The following examples are illustrative of representative embodiments of this invention and should not be construed to be limits on the scope or spirit of the instant invention.

The $R_f$ values cited were carried out on standard thin layer chromatography (TLC or tic) Si gel plates, with the elution solvent system used as indicated in each Example.

The fast atom bombardment (FAB) and electron impact (EI) mass spectral (MS) values are reported as molecular ion peaks and are indicated as either $M^+$, $MH^+$ or $MH^{++}$, being the molecular weight (mw), the molecular weight plus one atomic mass unit, or the molecular weight plus two atomic mass units.

The $^1H$ nuclear magnetic resonance (NMR) data was taken at 200 or 400 MHz and is tabulated for unique proton values of each compound at the end of the Examples.

EXAMPLE 1

Preparation of 17-(diphenylmethoxymethyl)-4-methyl-5-α- 4-azaandrostan-3-one

To a solution of 17-hydroxymethyl-4-methyl-5-α-4-azaandrostan- 3-one (0.096 g, 0.3 mM) and diphenyldiazomethane (0.25 g, 1.28 mM) in anhydrous methylene chloride (8 mL) at ice-bath temperatures was added boron trifluoride etherate (0.05 mL) dropwise over three minutes. The mixture was allowed to stir cold for an additional 25 minutes and then at ambient temperatures for 2 hours. The mixture was transferred to a separatory funnel with methylene chloride, washed with water, dried, and the methylene chloride removed in vacuo. Hash chromatography (silica gel, ethyl acetate as eluant) of the residue thus obtained yielded the title compound as a white waxy solid. Mass Spec (MS) M$^+$ calculated for $C_{33}H_{43}NO_2$, mw=485.71; observed m/e 485.

EXAMPLE 2

Preparation of 17-(carboethoxymethoxymethyl)-4-methyl- 5α-4-azaandrostan-3-one

Employing substantially the same procedure as described in Example 1, but substituting ethyl diazoacetate for the diphenyldiazomethane used therein, the title compound was obtained. MS M$^+$ calculated for $C_{24}H_{39}NO_4$, mw=405.58; observed m/e 405.

EXAMPLE 3

Preparation of 17-(carbobenzyloxymethoxymethyl)-4-methyl- 5α-4-azaandrostan-3-one Employing substantially the same procedure as described in Example 1, but substituting benzyl diazoacetate for the diphenyldiazomethane used therein, the title compound was obtained. MS MH$^+$ calculated for $C_{29}H_{41}NO_4$, mw=467.66; observed m/e 468.

EXAMPLE 4

Preparation of a) 20-(methoxymethyl)-4-methyl-5α-4-azapregnan-3-one and b) 20-(methoxy)-4-methyl-5α-4-azapregnan-3-one Employing substantially the same procedure as described in Example 1, but substituting 20-(hydroxymethyl)-4-methyl- 5-α-4-azapregnan-3-one and diazomethane in place of the corresponding steroid alcohol and diazo compound used in Example 1, title compound (a) was obtained as a white solid. MS M$^+$ calculated for $C_{23}H_{39}NO_2$, mw=361.57; observed m/e 361.

Employing substantially the same procedure as described in Example 1, but substituting 20-hydroxy-4-methyl-5α-4-azapregnan-3-one and diazomethane for the steroid alcohol and diazo compound used therein, title compound (b) was obtained. MS M+ calculated for $C_{22}H_{37}NO_2$, mw=347.54; observed m/e 347.

EXAMPLE 5

Preparation of 17-methoxymethyl-4-methyl-5α-4-azaandrostan-3-one

Employing substantially the same procedure as described in Example 4, but substituting 17-hydroxymethyl-5-α-4-azaandrostan-3-one for the steriod used therein, the title compound was obtained. MS M$^+$ calculated for $C_{21}H_{35}NO_2$, mw=333.53; observed m/e 333.

EXAMPLE 6

Preparation of 17-(ethylthiomethyl)-4-methyl-5α-4-azaandrostan-3-one

The mesylate of 17-hydroxymethyl-4-methyl-5-α-4-azaandrostan- 3-one (prepared from the alcohol and methanesulfonyl chloride in methylene chloride with pyridine at room temperature) (0.05 g, 0.125 mM) was heated with sodium thioethoxide (0.121 g, 1.44 mM) in anhydrous 1,2-dimethoxyethane in a nitrogen atmosphere for 73 hours. The solvent was removed in vacuo, the residue taken up in methylene chloride, washed (water) and dried. The residue obtained upon concentration of the methylene chloride was flash chromatographed (silica gel, ethyl acetate as eluant) to yield the title compound as a white waxy solid. MS MH$^+$ calculated for $C_{22}H_{37}NOS$, mw=363.60; observed m/e 364.

EXAMPLE 7

Preparation of 17-carboxymethoxymethyl-4-methyl-5-α-4-azaandrostan-3-one

The title compound was obtained by hydrolysis of 17-(carboethoxymethoxymethyl)- 4-methyl-5-α-4-azaandrostan-3-one using an aqueous-methanolic solution of NaOH. The title compound was also obtained by reduction of 17-(carbobenzyloxy-methoxymethyl)- 4-methyl-5-α-4-azaandrostan-3-one with hydrogen using palladium on carbon catalyst. MS MH$^+$ calculated for $C_{22}H_{35}NO_4$, mw=377; observed m/e 378.

EXAMPLE 8

Preparation of
a) 20-(diphenylmethoxy)4-methyl-5α-4-azapregnan-3-one, and
b) 20-(diphenylmethoxymethyl)4-methyl-5α-4-azapregnan-3-one The following compounds of formula 2 were made according to substantially the same procedure as described in Example 1, but substituting the 4-azapregnan-3-one starting material indicated below, for the 17-hydroxymethyl-4-methyl-5α-4-azaandrostan-3-one used therein:

a) 20-hydroxy-4-methyl-5α-4-azapregnan-3-one; MS M$^+$ calculated for $C_{34}H_{45}NO_2$, mw=499.72; observed m/e 499; and b) 20-hydroxymethyl-4-methyl-5α-4-azapregnan- 3-one; MS M$^+$ calculated for $C_{35}H_{47}NO_2$, mw=513.76; observed m/e 513.

EXAMPLE 9

Preparation of
a) 20-(ethylthiomethyl)-4-methyl-5α-4-azapregnan-3-one,
b) 20-(isopropylthiomethyl)4-methyl-5α-4-methyl- 5α-4-azapregnan-3-one, and
c) 17α-thiophenoxy-4-methyl-5α-4-azaandrostan-3-one Employing substantially the same procedure as described in Example 6, but substituting the 4-azaandrostan-3-one and thioethoxide starting materials used therein with the starting materials indicated below, the title compounds were obtained, except that to prepare title compound (c), DMF was used instead of $CH_2Cl_2$, and the reaction was heated for 3 hours to 170°–173° C.:

a) 20-hydroxymethyl-4-methyl-5α-4-azapregnan-3-one and Na$^+$SC$_2$H$_5$-; MS MH$^{++}$ calculated for $C_{24}H_{41}$NOS, mw=391.66; observed m/e 393;

b) 20-hydroxymethyl-4-methyl-5α-4-azapregnan-3-one and Na$^+$SCH(CH$_3$)$_2$-; MS MH$^+$ calculated for $C_{25}H_{43}$NOS, mw=405.68; observed m/e 406; and c) 17g-hydroxy-4-methyl-5α-4-azaandrostan-3-one and K$^+$SC$_6$H$_5$-. M.p. 187°–189° C.

EXAMPLE 10

Preparation of 17β-(4-nitrophenoxy)-4-methyl-5α-4-azaandrostan-3-one

To a stirred solution of 17β-hydroxy4-methyl-5α-4-azaandrostan-3-one (1.07 g, 3.5 mmole) and p-nitrofluorobenzene (2.0 ml, 18 mmole) in DMF (15 ml) under $N_2$ was added 95% NaH (180 mg, 7 mmole) in two portions during 10 mins. The mixture was stirred for 3 hours at room temperature and poured onto ice (50 g) and water (50 ml). The mixture was extracted with $CH_2Cl_2$ (30 ml×2). The organic layer was washed with brine and dried ($Na_2SO_4$). Removal of solvent gave the crude product which was purified via a flash silica gel column eluting with 1:1 ethyl acetate —$CH_2Cl_2$ to give the desired title product. Mp. 183°–184° C. (recrystallized from $CH_2Cl_2$-hexane).

EXAMPLE 11

Employing substantially the same procedure as described in Example 10 using 17β-hydroxy-4-methyl-5α-4-azaandrostan-3-one, compound 7 below, but substituting compound 8 for the p-nitrofluorobenzene used therein, and running the reaction at the temperature indicated, products of formula 9 were made, as defined in 11a—11e:

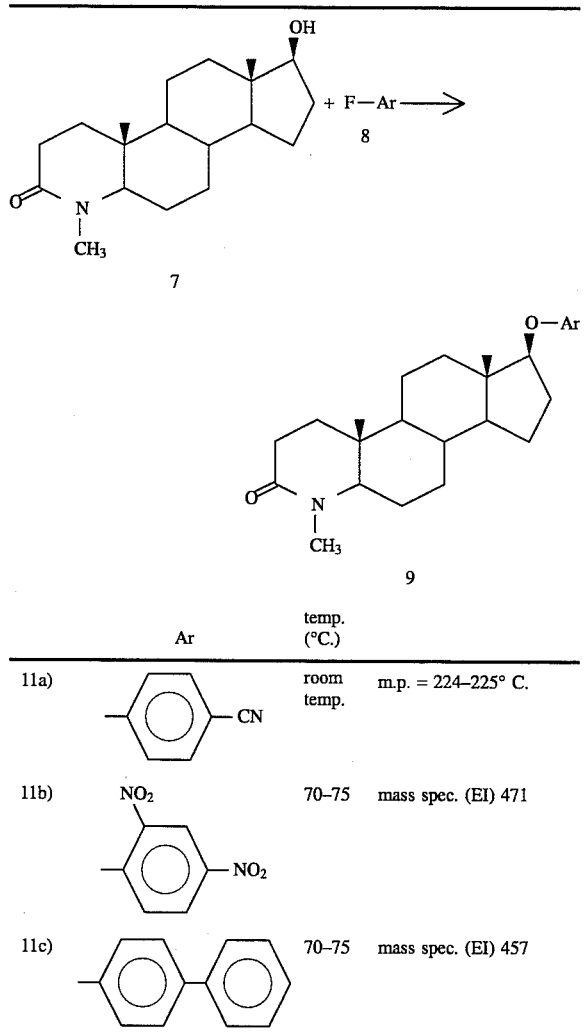

| | Ar | temp. (°C.) | |
|---|---|---|---|
| 11a) | —C6H4—CN | room temp. | m.p. = 224–225° C. |
| 11b) | —C6H3(NO2)2 | 70–75 | mass spec. (EI) 471 |
| 11c) | —C6H4—C6H5 | 70–75 | mass spec. (EI) 457 |
| 11d) | pyridyl | 70–75 | m.p. 172–174° C. |
| 11e) | —C6H4—CH=CH2 | 70–75 | mass spec. (FAB) 408 |

The following products of formula 9, as deemed in 11f–11b, were made using substantially the same procedure as described above, except that in place of NaH/DMF, for 11f KOH/DMF was used, and for 11g–11h KOH/DMSO was used and the reactions were stirred for about 20 hours at 70°–80° C. instead of for 3 hours at room temperature:

| | Ar | |
|---|---|---|
| 11f) | —C6H4—Br | mass spec. (FAB) 460 |
| 11g) | —C6H4—Cl | mass spec. (FAB) 416 |
| 11h) | —C6H4—CH3 | m.p. 176–179° C. |

EXAMPLE 12

Preparation of 17β-(4-aminophenoxy)-4-methyl- 5α-4-azaandrostan-3-one hydrochloride 17β-(4-nitrophenoxy)-4-methyl-5α-4-azaandrostan-3-one (938 mg, 2.2 mmole) in MeOH (70 ml) was hydrogenated at 40 psi in the presence of $PtO_2$ (400 mg) for 90 mins. To the resulting mixture was added 5% conc. HCl in absolute ethanol (4 ml) under $N_2$, and then the mixture was filtered through a pad of celite. The filtrate was concentrated, vacuum dried, and then triturated with $CH_2Cl_2$-hexane to give the title product, mp. 307°–310° C.

EXAMPLE 13

Preparation of 17β-(4-acetamidophenoxy)-4-methyl-5α-4-azaandrostan-3-one

To 17β-(4-aminophenoxy)-4-methyl- 5α-4-azaandrostan-3-one hydrochloride (7mg) in $CH_2Cl_2$ (100 μl) was added acetic anhydride (30 μl) followed by adding pyridine (50 μl). The mixture was stirred at room temperature for 2 hr and then concentrated to dryness. The residue was purified via a silica gel plate developed with 5% MeOH— EtOAc ($R_f$=0.3) to give the title product, mp. 340° C.

EXAMPLE 14

Preparation of 17β-(4-carboxamidophenoxy)4-methyl-5α-4-azaandrostan- 3-one

To a solution of 17β-(4-cyanophenoxy)-4-methyl-5α-4-azaandrostan-3-one (102 mg, 0.25 mmole) in absolute ethanol (0.80 ml) and THF (0.40 ml) was added 30% $H_2O_2$ (0.20 ml) and then 5N NaOH (0.12 ml) dropwise. The resulting mixture was stirred at 48–50° C for 5 hr. and concentrated to a residue. The residue was taken up in methylene chloride and purified via preparative silica gel plate ($R_f$=0.3; 10% MeOH—EtOAc) to yield the title compound, mp 313°–315° C.

EXAMPLE 15

Preparation of a) 17β-phenoxy-4-methyl-5α-4-azaandrostan-3-one, b) 17α-phenoxy4-methyl-5α-4-azaandrostan-3-one and c) 17α-(4-biphenyloxy)-4-methyl-5α-4-azaandrostan-3-one To a mixture of 17β-(4-aminophenoxy)4-methyl- 5α-4-azaandrostan- 3-one hydrochloride (49 mg) in conc. $H_2SO_4$-95% EtOH (80 ml, 1:4 v/v) at 5°–10° C. was added 95% EtOH (0.75 ml) and ice (0.25 g) with stirring. To this suspension at 5° C. was added a solution of $NaNO_2$ (12.5 mg) in $H_2O$ (21.5 μl) over 10 min. After stirring at 5° C. for 1 hr, additional 95% EtOH (1.0 ml) was added and the reaction stirred at 5° C. for 20 min to increase the solubility and the diazotization process. To this mixture was added ether washed copper bronze (5 mg) and the mixture was heated at reflux for 5 min. The mixture was then purified on a silica gel plate developed with EtOAc ($R_f$=0.25, EtOAc) to yield the title product (a). m.p. 169.5°–171° C.

The title product (b) was prepared by combining 17β-hydroxy- 4-methyl-5α-4-azaandrostan-3-one (61 mg., 0.20 mmol), phenol (57.4 mg, 0.60 mmol), $Ph_3P$ (68 mg, 0.26 mmol), and DEAD (43 μl, 0.26 mmol) in dry THF (1.0 ml) in a test tube under $N_2$, and heating the mixture to 80° C. After 2 hours, TLC showed that about 3–5% starting material remained in the reaction mixture. The mixture was purified via preparative TLC in a silica gel plate (1500μ) developed with 4% MeOH/$CH_2Cl_2$ first and then after drying, with 33% MeOH/$CH_2Cl_2$, to obtain the crude product (b). The crude material was re-purified via preparative TLC, each on a separate silica gel plate (1000 g) developed with EtOAc. The product was obtained from both plates, and triturated with 5% $CH_2Cl_2$/hexane to yield the title compound (b).

The title product (c) was prepared using essentially the same procedure as described for making title product (b), except substituting 4-hydroxybiphenyl for the phenol used therein. $R_f$=0.3, EtOAc; m.p. 219°–222° C.

EXAMPLE 16

Preparation of 17β-hexloxy-4-methyl-5α-4-azaandrostan-3-one

To a solution of 17β-hydroxy-4-methyl-5α-4-azaandrostan- 3-one (102 mg, 0.336 mmol) in DMSO (3 ml) was added powdered KOH (300 mg) followed by n-hexyliodide (400 μl). After stirring the reaction mixture overnight, the reaction was diluted with water and extracted with ethyl acetate. The organic layer was washed with water, then brine, then dried (MgSO$_4$), and concentrated in vacuo. The residue was then purified by preparative thin layer chromatography to afford the title compound, characterized by $H^1$ NMR.

Employing substantially the same procedure using KOH/ DMSO as described above, but substituting compounds 10 and 11, below, for the steroid and the n-hexyl iodide, respectively, used therein, the following products of formula 12 were made, as defined in 16a–16f:

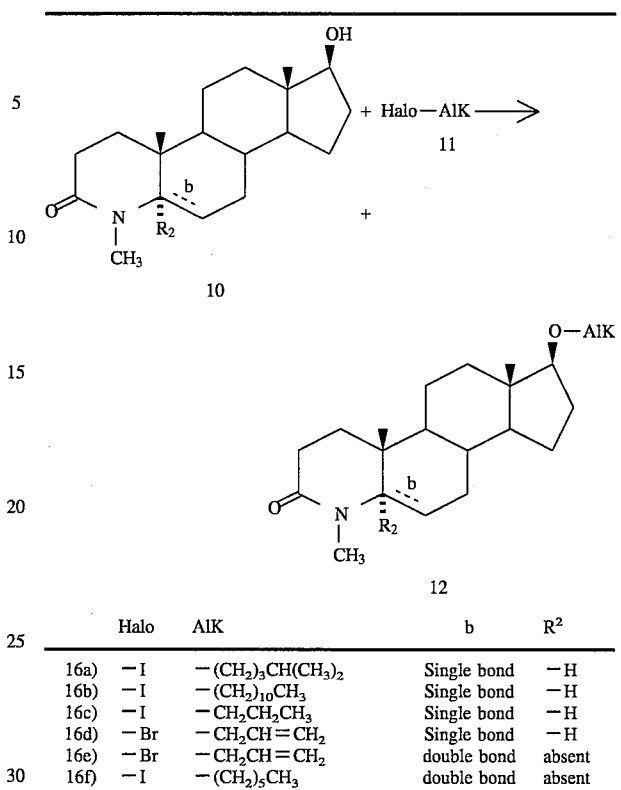

| | Halo | Alk | b | $R^2$ |
|---|---|---|---|---|
| 16a) | —I | —(CH$_2$)$_3$CH(CH$_3$)$_2$ | Single bond | —H |
| 16b) | —I | —(CH$_2$)$_{10}$CH$_3$ | Single bond | —H |
| 16c) | —I | —CH$_2$CH$_2$CH$_3$ | Single bond | —H |
| 16d) | —Br | —CH$_2$CH=CH$_2$ | Single bond | —H |
| 16e) | —Br | —CH$_2$CH=CH$_2$ | double bond | absent |
| 16f) | —I | —(CH$_2$)$_5$CH$_3$ | double bond | absent |

EXAMPLE 17

Preparation of 50α-4-azaandrostan-3-on-17β-yloxyacetic acid

Step A: Preparation of testosterone-seco-acid ethyl ester

Testosterone-seco-acid (24.0 g) and toluene-sulfonic acid monohydrate (0.5 g) in absolute ethanol were refluxed for 3 hours. Removal of solvent gave the crude ethyl ester which was used in Step B without purification.

Step B: Preparation of diethyl ester of testosterone-seco-acid-17β-yloxyacetic acid To the ethyl ester (19 g, from Step A) in methylene chloride (200 ml) was added over a 5 hour period a solution of ethyl diazoacetate (7.6 ml) in methylene chloride (40 ml), and solid rhodium diacetate dimer (40 mg) was added in 10 portions during 5 hours, which resulted in ca. 50% conversion to the desired product. The mixture was concentrated to a residue which was purified by two silica gel flash column chromatography to give the liquid title compound.

Step C: Preparation of testosterone-seco-acid-17β-yloxyacetic acid

To the diethyl ester (10.0 g, from Step B) in methanol (210 ml) and THF (210 ml) was added 5N NaOH (50 ml) dropwise during 30 min. This mixture was stirred for another 15 minutes and filtered. The filtrate was concentrated, and extracted with methylene chloride to remove non-acid impurities. The aqueous solution was acidified with 6N HCl to pH 2 and extracted with $CH_2Cl_2$. The organic layer was dried ($Na_2SO_4$) and concentrated to give the title diacid.

Step D: Preparation of 4-azaandrost-5-en-3-on-17β-yloxyacetic acid

The diacid (6.0 g, from Step C) in glacial acetic acid (52 ml) and methylene chloride (16 ml) was charged with ammonium acetate (6.4 g). The mixture was heated at 122°–125° C. for 3 hours and distilled off 17 ml of distillate. The reaction solution was stirred at 80° C. while adding deionized (DI) water (70 ml) dropwise during 30 min. The mixture was stirred at 60°–70° C. for 15 minutes, at room temperature for 15 min, and at 0° C. for 30 minutes. The solid product was collected and dried.

Step E: Preparation of 5α-4-azaandrostan-3-on-17β-yloxyacetic acid

The unsaturated acid (3.2 g, from Step D) in glacial acetic acid (200 ml) and platinum oxide (1.0 g) was hydrogenated at 60° C. under 40 psi for 24 hours. The mixture was filtered through a pad of celite, and the filtrate concentrated to dryness. The residue was recrystallized from 5% MeOH in methylene chloride to yield the title acid.

EXAMPLE 18

Preparation of a) 5α-4-azaandrostan-3-on- 17β-yloxy-N-(4-acetylphenyl)acetamide, b) 17β-methyleneoxy-[N-cyclohexyl-N-(N-cyclohexylcarbamoyl)carbamoyl]- 5α-4-azaandrostan-3 -one, and c) 5α-4-azaandrostan-3-on-17β-yloxy-N-phenylacetamide To a mixture of 5α-4-azaandrostan-3-on-17β-yloxy acetic acid (280 mg) and 4-aminoacetophenone (200 mg) in methylene chloride (50 ml) was added DCC (500 mg) and DMAP (40 mg). The mixture was stirred at ambient temperature for 3 hours, and filtered. The filtrate was concentrated to a residue which was purified via preparative thin layer chromatography (TLC) on three silica gel plates (1000μ) developed with 5.5% MeOH in EtOAc twice to give the title acetamide (a) ($R_f$=0.33; top. 252°–254° C.) and the title carbamate (b) ($R_f$=0.51).

Employing substantially the same procedure, but substituting aniline for the 4-aminoacetophenone, the title acetamide (c) (m.p. 263°–265° C.) and the title carbamate (b) were obtained.

EXAMPLE 19

Preparation of a) 5α-4-azaandrostan- 3-on-17β-yloxy-N-(4-t-butylphenyl)acetamide and b) 17β-methyleneoxy-[N-isopropyl-N-(N-isopropylcarbamoyl)carbamoyl]- 5α-4-azaandrostan-3-one To a mixture of 5α-4-azaandrostan-3-on-17β-yloxy acetic acid (90 mg) and 4-t-butylaniline (80 mg) in DMF (3 ml) and methylene chloride (3 ml) was added DIC (100 mg) and DMAP (15 mg). The mixture was stirred at room temperature for 18 hours, and poured onto ice-water. The mixture was extracted with methylene chloride and dried ($Na_2SO_4$). Removal of solvent gave the crude products which were purified via preparative TLC on three silica gel plates (1000 m) developed with 2–5% MeOH in $CH_2Cl_2$ about 5 times to give the title amide (a) (higher $R_f$; mp 266°–268° C.) and the carbamate (b) (lower $R_f$; mp 133°–137° C.).

EXAMPLE 20

Preparation of 5α-4-azaandrostan-3-on- 17β-yloxy-N-[4-1'(RS)-hydroxyethylphenyl]acetamide To 5α-4-azaandrostan-3-on-17β-yloxy-N-(4-acetylphenyl)acetamide (20 mg) in methanol (5 ml) at 10°–15° C. was added $NaBH_4$ (18 mg) in portions during 10 minutes. The mixture was stirred in the cold for 60 minutes and purified using two silica gel plates (1000μ) developed with 9% MeOH in $CH_2Cl_2$ to give the title compound ($R_f$=0.41; mp 281°–283° C.).

EXAMPLE 21

Preparation of ethyl 5α-4-azaandrostan-3-on- 17β-yloxyacetate

Step A: Preparation of 4-N-benzoyl-17β-t-butyl-dimethylsilyloxy- 4-azaandrost-5-en-3-one To 17β-t-butyldimethylsilyloxy-4-azaandrost-5-en-3-one (2 g) in pyridine (5 ml) at 5°–10° C. was added benzoyl chloride (2 ml) in $CH_2Cl_2$ (10 ml) dropwise. After the addition, the mixture was stirred at 60° C. for 3 hours and poured onto ice-water. The mixture was extracted with methylene chloride, and dried ($Na_2SO_4$). Removal of solvent gave the crude product which was recrystallized from $CH_2Cl_2$-hexane to afford the title product.

Step B: Preparation of 4-N-benzoyl-17β-hydroxy- 4-azaandrost-5-en-3one

To the product of Step A, above, (2.0 g) in THF (80 ml) in a polyethylene bottle was added hydrofluoric acid (2.0 ml) dropwise. The mixture was sitrred at room temperature until the reaction was complete. The mixture was neutralized with saturated sodium bicarbonate solution until slightly alkaline. The mixture was concentrated, and extracted with methylene chloride. The organic layer was dried ($Na_2SO_4$), and concentrated to a residue which was purified via flash silica gel column chromatography eluted with 40–50% EtOAc in hexane to give the title product.

Step C: Preparation of 4-N-benzoyl-4-azaandrost- 5-en-3-on-17β-yloxyacetic acid ethyl ester To the alcohol product from Step B, above and ethyl diazoacetate (0.5 ml) in methylene chloride (6.5 ml) was added rhodium diacetate dimer (15 mg) intermittently during 2 hours. The mixture was stirred at room temperature for 18 hours. The mixture was concentrated and the residue was purified via preparative TLC using two silica gel plates (2000μ) developed with 40% EtOAc in hexanes to afford the title compound ($R_f$=0.33).

Step D: Preparation of 4-azaandrost-5-en-3-on-17β-yloxyacetic acid ethyl ester

To the product of Step C, above, (90 mg) in $CH_2Cl_2$ (2.0 ml) was added hydrazine hydrate (0.2 ml). The mixture was shaken for a few minutes and purified via preparative TLC using two silica gel plates (1500μ) developed with EtOAc to give the title product ($R_f$=0.54).

Step E: Preparation of ethyl 5α-4-azaandrostan- 3-en-17β-yloxyacetate

The product of Step D, above, and platinum oxide (35 mg) in glacial acetic acid (2 ml) was hydrogenated at 40 psi for 22.5 hours. The mixture was filtered through a pad,of celite. The filtrate was concentrated and the residue purified via preparative TLC using one silica gel plate (1000μ) developed with EtOAc to give the title product ($R_f$=0.22; mp 170°–172° C.).

EXAMPLE 22

Preparation of ethyl 4-methyl-5α-4-azaandrostan- 3-on-17β-yloxyacetate

To a solution of 17β-hydroxy4-methyl- 5α-4-azaandrostan- 3-one (2.37 g, 7.75 mmole) in methylene chloride (50 ml) was added ethyl diazoacetate (5.5 g, 48 mmole) and rhodium diacetate dimer (50 mg) intermittently in small portions during 60 hours resulting in ca. 35% conversion to product. The mixture was passed through a flash silica gel column eluted with 1.5% MeOH in $CH_2Cl_2$ to give the semi-purified product which was repurified via another flash silica gel column eluted with 60–95% EtOAc in hexane to give the title product, ($R_f$0.3/EtOAc) mp. 39°–41° C.

EXAMPLE 23

Preparation of 4-methyl-5α-4-azaandrostan-3-on-17β-yloxyacetic acid

To ethyl 4-methyl-5α-4-azaandrostan-3-on-17β-yloxyacetate (275 mg) in THF (10 ml) and MeOH (5 ml) under $N_2$ was added 2N NaOH (3.0 ml). The mixture was stirred at room temperature for 2 hours, then concentrated in vacuo. The aqueous residue was extracted with $CH_2Cl_2$. The aqueous layer was then acidified with 3.0 N HCl (ca. 2.1 ml) to pH 2, and extracted with $CH_2Cl_2$. The organic layer was washed with brine and dried ($Na_2SO_4$). The solvent was removed, and the crude product recrystallized from $CH_2Cl_2$/hexane to give the title compound. m.p. 180.5°–184° C.

EXAMPLE 24

Preparation of a) diphenylmethyl 4-methyl- 5α-4-azaandrostan-3-on-17β-yloxyacetate and b) diphenylmethyl-5α-4-azaandrostan-3-on-17β-yloxyacetate To 4-methyl-5α-4-azaandrostan-3-on-17β-yloxyacetic acid (3.5 mg) in $CH_2Cl_2$ (0.2 ml) under $N_2$ was added diphenyldiazomethane (ca. 20 mg) in portions during 15 minutes. The reaction stirred at room temperature for 2 hours, then additional diphenyldiazomethane (ca. 5 mg) was added and the reaction was allowed to stir overnight. The mixture was purified via preparative TLC on a silica gel plate (1000μ) developed with EtOAc to yield diphenylmethyl 4-methyl-5α-4-azaandrostan-3-on-17β-yloxyacetate, ($R_f$=0.4/EtOAc).

Employing substantially the same procedure as described above, but substituting 5α-4-azaandrostan-3-on-171β-yloxyacetic acid for the starting acid used therein, diphenylmethyl 5α-4-azaandrostan-3-on- 17β-yloxyacetate was obtained.

EXAMPLE 25

Preparation of a) 4-methyl-5α-4-azaandrostan- 3-on-17β-yloxy-N-(3,4-dichlorobenzyl)acetamide and b) 4-methyl-5α-4-azaandrostan-3-on- 17β-yloxy-N-phenylacetamide Ethyl 4-methyl-5α-4-azaandrostan-3-on-17β-yloxyacetate (30 mg, ca. 70% pure) and 3,4-dichlorobenzylamine (0.3 ml) were heated together under $N_2$ at 172° C. for 18 hours. The mixture was purified via preparative TLC on a silica gel plate (2000μ) developed with EtOAc to yield the crude dichlorobenzylacetamide compound. The crude product was dissolved in $CH_2Cl_2$ and filtered, and the solvent removed in vacuo, and the residue was re-purified via preparative TLC on a silica gel plate (500μ) to yield the dichlorobenzylacetamide title product (a). MS $M^+$ calculated for $C_{28}H_{38}Cl_2N_2O_3$, MW=521.53; observed m/e 520, 521, 522.

Employing substantially the same procedure as described above, but substituting aniline for the amine used therein, and stirring the mixture for ca. 81 hours instead of 18 hours, the phenylacetamide title product (b) was obtained, ($R_f$=0.4 in 6:7 acetone:EtOAc), m.p. 221°–223° C.

EXAMPLE 26

Preparation of 5α-4-azaandrostan- 3-on-17β-yloxy-N-(4-acetylphenyl)acetamide via mixed anhydride method To a mixture of 5α-4-azaandrostan-3-on-17β-yloxyacetic acid (175 mg) and N-methylmorpholine (60 μl) in dry THF (80 ml) was stirred at room temperature for ½ hour and then cooled to −20° C. under $N_2$. To this mixture was added isobutyl chloroformate (75 ml) dropwise during 5 min. period and stirred at −20° C. for 20 min. followed by adding a solution of 4-amino-acetophenone (100 mg) in THF (3 ml) dropwise. The mixture was stirred at −20° C. for ½ hr and then at ambient temperature overnight. The mixture was concentrated and purified via preparative TLC developed with 11% MeOH in EtOAc to give the title product.

EXAMPLE 27

Preparation of a) 4-methyl-17α-phenylsulfonyl- 5α-4-azaandrostan-3-one and b) 4-methyl-17α-phenylsul-finyl-5α-4-azaandrostan-3-one isomer a and isomer b To 17α-thiophenoxy-4-methyl-5α-4-aza-androstan-3-one (65 mg) in $CH_2Cl_2$ (5 ml) was added a solution of MCPBA (53 mg) in $CH_2Cl_2$ (1 ml) dropwise. The mixture was stirred at room temperature for 1 hour and subjected to preparative TLC purification using two silica gel plates (2000μ) developed with EtOAc twice ($R_f$=0.39; 0.18; 0.11/EtOAc×2). Repurification via peparative TLC afforded the title sulfone (a) ($R_f$=0.44/EtOAc×2; mp. 265°–268° C.) and the title sulfoxide (b) isomer a ($R_f$=0.19/EtOAc×2; mp. 180°–181.5° C.) and the sulfoxide (b) isomer b ($R_f$=0.12/EtOAc×2; mp 199°–201° C.).

EXAMPLE 28

Preparation of a) 17β-(2-picolyloxy)-4-methyl-5α-4-azaandrostan-3-one and b) 17β-benzyloxy-4-methyl-5α-4-azaandrostan-3-one To 17β-hydroxy-4-methyl-5α-azaandrostan-3-one (61 mg) in THF (4 ml) was added 95% NaH (20 mg) and 2-picolyl chloride hydrochloride (82 mg) under $N_2$. The mixture was heated at 70°–80° C. for 18 hours. The mixture was purified viii silica gel preparative TLC to give the title compound (a) ($R_f$=0.20/EtOAc×2; mp. 171°–173° C.).

Using benzyl bromide in place of 2-picolylchloride in the above procedure gave the title benzyloxy compound (b) ($R_f$=0.39/EtOAc×2; mp. 198°–199° C.).

EXAMPLE 29

Preparation of a) 17β-diphenylmethoxy-4-methyl-5α-4-azaandrostan-3-one and b) 17β-diphenylmethoxy-5α-4-azaandrostan-3-one To a stirred solution of 17β-hydroxy-4-methyl-5α-4-azandrostan-3-one (25 mg) and $BF_3$•etherate (2 drops) in THF (1.5 ml) was added intermittently diphenyldiazomethane (5 mg×4). Preparative TLC purification of the mixture using a silica gel plate developed with EtOAc yielded title compound (a) ($R_f$=0.4/EtOAc); m.p. 79°–82° C.

Title compound (b) was prepared using substantially the same procedure as described for title compound (a), except 17β-hydroxy- 5α-4-azaandrostan-3-one was used as the starting material.

EXAMPLE 30

Preparation of
a)  4-methyl-5α-4-azaandrostan-3-on-17β-yloxy-N-(4-acetylphenyl)acetamide, and
b)  17β-methyleneoxy-[N-cyclohexyl-N-(N-cyclohexylcarbamoyl)carbamoyl]- 4-methyl-5α-4-azaandrostan-3-one To 4-methyl-5α-4-azaandrostan-3-on-17β-yloxy acetic acid (43 mg) and acetylaniline (50 mg) in CH$_2$Cl$_2$ (2.5 ml) was added DCC (150 mg) and DMAP (5 mg) with stirring at room temperature for 18 hours. Silica gel preparative TLC purification (R$_f$= 0.15/EtOAc) gave title compound (a) with m.p. 171.5°–173° C., and title compound (b) (R$_f$=0.25/EtOAc).

EXAMPLE 31

Preparation of 4-methyl-5α-4-azaandrostan-3-on-17β-yloxyacetamide

4-Methyl-5α-4-azaandrostan-3-on-17β-yloxyacetic acid (40 mg) and formamide (0.8 ml) were heated at 178°–180° C. under N$_2$ for 18 hours. The mixture was cooled to room temperature and poured onto ice-water. The crude product was extracted with CH$_2$Cl$_2$ and dried (Na$_2$SO$_4$). Removal of solvent gave the crude product which was recrystallized from CH$_2$Cl$_2$-hexane with trace MeOH to give title product, m.p. 222°–225° C.

EXAMPLE 32

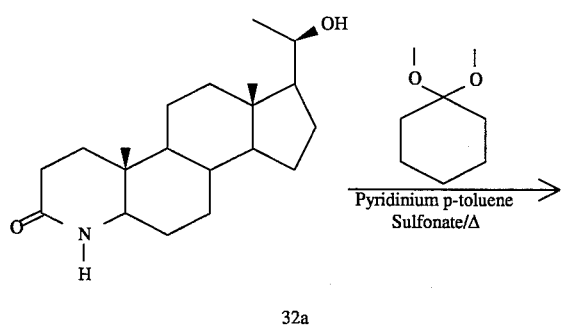

32a

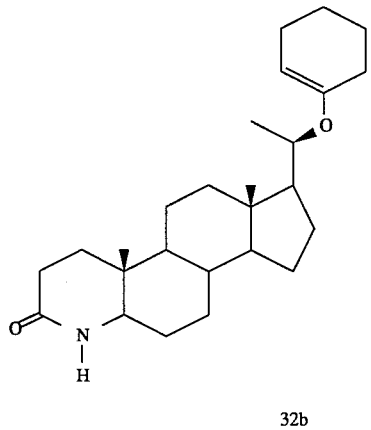

32b

To a solution of azasteroid 32a (250 mg) in dimethoxy-cyclo-hexane (10 ml) was added pyridinum p-toluene-sulfonate and the reaction mixture was heated at 140° C. for 2 hrs. The temperature of the reaction was increased and dimethoxycyclohexane was removed slowly by distillation over 4 hrs. Finally all the dimethoxycyclohexane was distilled off and residue taken in ethyl acetate, washed with aqueous sodium bicarbonate, brine, dried and concentrated to give 32b. MS calculated for C$_{27}$H$_{43}$NO$_2$, 413.65. Observed 413 (EI).

EXAMPLE 33

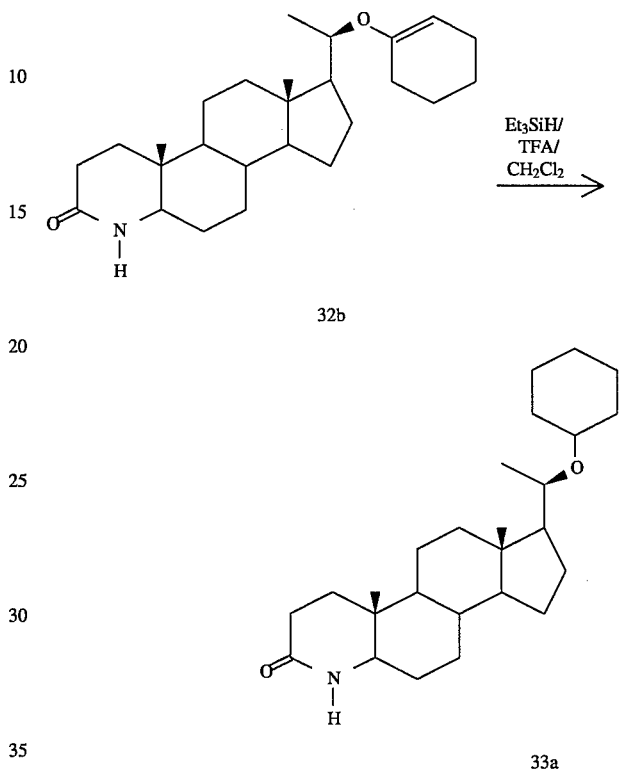

33a

To a solution of enol ether 32b (150 mg) in CH$_2$Cl$_2$ (2 ml) was added triethylsilane (418.6 mg, 10 eq.) followed by slow dropwise addition of trifluoroacetic acid (TFA) (2.07 g). After stirring the reaction overnight at room temperature, the reaction mixture was diluted with CH$_2$Cl$_2$, washed with aq. NaHCO$_3$, brine, dried and concentrated. The residue was purified by preparative thin layer chromatography over silica gel using 30% acetone/CH$_2$Cl$_2$ as solvent to obtain 33a. MS calculated for C$_{27}$H$_{45}$NO$_2$, 415.66. Observed 415(EI).

Also included with the scope of this invention are 4-N-X analogs wherein X is OH, NH$_2$ or SCH$_3$. The 4-N-OH and 4-N-NH$_2$ derivatives can be made by incorporating hydroxylamine or hydrazine, respectively, in place of methyl amine in the seco acid ring A closure for the starting androstanes herein as described in J. Med. Chem. 29, 998-2315 (1986) by Rasmusson et al. Further, reaction of the anion of the saturated 4-N-H androstanes, wherein the anion is generated from the 4-NH precursor by sodium hydride, and methyl sulfenyl chloride can produce the corresponding 4-N-SCH$_3$ derivative. Thus, substituent R$^3$ on the 4-N position also includes OH, NH$_2$ and SCH$_3$.

| | NMR DATA | |
|---|---|---|
| Example | Angular Methyls(ppm) | Miscellaneous(ppm) |
| 1 | 0.58, 0.88 | 5.28 (—OC$\underline{H}$(Ph)$_2$) |
| 2 | 0.66, 0.89 | 1.29 (C$\underline{H}_3$CH$_2$OCO) |

-continued

NMR DATA

| Example | Angular Methyls(ppm) | Miscellaneous(ppm) |
|---|---|---|
| 3 | 0.64, 0.89 | 5.49 (—COOC$\underline{H}$$_2$Ph) |
| 4a | 0.69, 0.88 | 3.31 (—CH$_2$OC$\underline{H}$$_3$) |
| 4b | 0.69, 0.89 | 3.28 (—OC$\underline{H}$$_3$) |
| 5 | 0.64, 0.89 | 3.32 (—CH$_2$OC$\underline{H}$$_3$) |
| 6 | 0.64, 0.89 | 1.25 (—CH$_2$SCH$_2$C$\underline{H}$$_3$) |
| 7 | 0.67, 0.89 | 4.07 (—CH$_2$OC$\underline{H}$$_2$COOH) |
| 8a | 0.56, 0.84 | 5.29 (—OC$\underline{H}$(Ph)$_2$) |
| 8b | 0.68, 0.88 | 5.28 (—CH$_2$OC$\underline{H}$(Ph)$_2$) |
| 9a | 0.68, 0.88 | 1.25 (—CH$_2$SC$\underline{H}$$_2$CH$_3$) |
| 9b | 0.68, 0.88 | 1.24 (—CH$_2$SCH(C$\underline{H}$$_3$)$_2$) 1.27 |
| 9c | 0.90, 0.93 | 2.94 (-4-NC$\underline{H}$$_3$) |
| 10 | 0.92, 0.95 | 2.93 (-4-NC$\underline{H}$$_3$) |
| 11a | 0.91, 0.93 | 2.93 (-4-NC$\underline{H}$$_3$) |
| 11b | 0.93, 0.99 | 2.94 (-4-NC$\underline{H}$$_3$) |
| 11c | 0.93, 0.97 | 2.95 (-4-NC$\underline{H}$$_3$) |
| 11d | 0.91, 0.93 | 2.93 (-4-NC$\underline{H}$$_3$) |
| 11e | 0.91 (6H) | 2.93 (-4-NC$\underline{H}$$_3$) |
| 11f | 0.91 (6H) | 2.93 (-4-NC$\underline{H}$$_3$) |
| 11g | 0.92 (6H) | 2.92 (-4-NC$\underline{H}$$_3$) |
| 11h | 0.91 (6H) | 2.27 (Ph—C$\underline{H}$$_3$) |
| 12 | 0.92, 0.94 | 2.98 (-4-NC$\underline{H}$$_3$) |
| 13 | 0.92 (6H) | 2.15 (—NHCOC$\underline{H}$$_3$) |
| 14 | 0.91, 0.93 | 2.93 (-4-NC$\underline{H}$$_3$) |
| 15α | 0.91, 0.93 | 2.93 (-4-NC$\underline{H}$$_3$) |
| 15b | 0.82, 0.92 | 2.95 (-4-NC$\underline{H}$$_3$) |
| 15c | 0.83, 0.91 | 2.94 (-4-NC$\underline{H}$$_3$) |
| 16(title) | 0.74, 0.87 | 2.91 (-4-NC$\underline{H}$$_3$) |
| 16a | 0.76, 0.89 | 2.92 (-4-NC$\underline{H}$$_3$) |
| 16b | 0.76, 0.89 | 2.92 (-4-NC$\underline{H}$$_3$) |
| 16c | 0.76, 0.88 | 2.92 (-4-NC$\underline{H}$$_3$) |
| 16d | 0.80, 0.88 | 2.92 (-4-NC$\underline{H}$$_3$) |
| 16e | 0.80, 1.10 | 3.10 (-4-NC$\underline{H}$$_3$) |
| 16f | 0.78, 1.10 | 3.10 (-4-NC$\underline{H}$$_3$) |
| 17, Step A | 0.94, 1.15 | 1.27 (t) (—OCH$_2$C$\underline{H}$$_3$) |
| 17, Step B | 0.88, 1.14 | 1.27 (t) (—OCH$_2$C$\underline{H}$$_3$) 1.30 (t) (—OCH$_2$C$\underline{H}$$_3$) |
| 17, Step C | 0.89, 1.15 | 4.16 (—OC$\underline{H}$$_2$COOH) |
| 17, Step D | 0.86, 1.10 | 4.12 (dd) (—OC$\underline{H}$$_2$COOH) |
| 17, Step E | 0.82, 0.90 | 4.11 (dd) (—OC$\underline{H}$$_2$COOH) |
| 18a | 0.89, 0.94 | 2.60 (—COC$\underline{H}$$_3$) |
| 18b | 0.81, 0.91 | |
| 18c | 0.86, 0.92 | |
| 19a | 0.86, 0.93 | 1.31 (—C(C$\underline{H}$$_3$)$_3$) |
| 19b | 0.82, 0.92 | 1.22 (d) (—CH(C$\underline{H}$$_3$)$_2$) 1.44 (d) (—CH(C$\underline{H}$$_3$)$_2$) |
| 20 | 0.86, 0.91 | 1.48 (d) (—CH(OH)C$\underline{H}$$_3$) |
| 21, Step A | 0.87, 1.31 | 0.91 (—C(C$\underline{H}$$_3$)$_3$) |
| 21, Step B | 0.80, 1.30 | |
| 21, Step C | 0.85, 1.30 | 4.09 (—OC$\underline{H}$$_2$CO$_2$Et) |
| 21, Step D | 0.86, 1.12 | 4.10 (—OC$\underline{H}$$_2$CO$_2$Et) |
| 21, Step E | 0.80, 0.88 | 4.09 (—OC$\underline{H}$$_2$CO$_2$Et) |
| 22 | 0.82, 0.90 | 2.92 (-4-NC$\underline{H}$$_3$) |
| 23 | 0.82, 0.90 | 2.94 (-4-NC$\underline{H}$$_3$) |
| 24a | 0.80, 0.89 | 2.92 (-4-NC$\underline{H}$$_3$) |
| 24b | 0.79, 0.89 | 4.18 (—OC$\underline{H}$$_2$CO$_2$CHPh$_2$) |
| 25α | 0.76, 0.87 | 2.91 (-4-NC$\underline{H}$$_3$) |
| 25b | 0.87, 0.92 | 2.93 (-4-NC$\underline{H}$$_3$) |
| 26 | 0.89, 0.93 | 4.08 (—OC$\underline{H}$$_2$CO—) |
| 27a | 0.89, 0.93 | 2.94 (-4-NC$\underline{H}$$_3$) |
| 27b (Isom. a) | 0.90, 0.92 | 2.94 (-4-NC$\underline{H}$$_3$) |
| 27b (Isom. b) | 0.92, 0.98 | 2.95 (-4-NC$\underline{H}$$_3$) |
| 28a | 0.87, 0.91 | 2.93 (-4-NC$\underline{H}$$_3$) |
| 28b | 0.86, 0.91 | 4.54 (—C$\underline{H}$$_2$Ph) |
| 29a | 0.91, 0.93 | 5.42 (Ph$_2$C$\underline{H}$O—) |
| 30a | 0.89, 0.93 | 2.60 (—COC$\underline{H}$$_3$) |
| 30b | 0.80, 0.88 | 2.92 (-4-NC$\underline{H}$$_3$) |
| 31 | 0.80, 0.89 | 2.93 (-4-NC$\underline{H}$$_3$) |

Novel compounds of this invention also include, but are not limited to, the following compounds. These compounds can be prepared according to the procedures in the Examples indicated below, using the appropriate starting materials.

| Prepared by Example | |
|---|---|
| 16 | 4-methyl-17-(3-methylbutyloxymethyl)-5α-4-azaandrostan-3-one, |
| 16 | 4-methyl-20-(3-methylbutyloxymethyl)-5α-4-azapregnan-3-one, |
| 18 | 4-methyl-17-(N-phenylcarboxamidomethoxymethyl)-5α-4-azaandrostan-3-one, |
| 10 | 4-methyl-17-(p-nitrophenoxymethyl)-4-methyl-5α-4-azaandrostan-3-one, 17-(p-(dimethylamino)phenoxymethyl)-4-methyl-5α-4-azaandrostan-3-one, |
| 9 | 24-(isopropylthio)-4-methyl-5α-4-azacholan-3-one, 4-methyl-17-(p-trimethylammonium)phenoxymethyl)-5α-4-azaandrostan-3-one iodide, |
| 9 | 17-(3-(isopropylthio)propyl)-4-methyl-5α-4-azaandrostan-3-one, |
| 16 | 17-(allyloxymethyl)-4-methyl-5α-4-azaandrostan-3-one, |
| 16 | 4-methyl-17-(n-propyloxymethyl)-5α-4-azaandrostan-3-one, |
| 16 | 20-(allyloxymethyl)-4-methyl-5α-4-azapregnan-3-one, |
| 25 | N-phenyl 4-methyl-5α-22-oxa-3-oxo-4-azacholanamide, |
| 26 | N-(4-acetylphenyl) 4-methyl-5α-22-oxa-3-oxo-4-azacholanamide, |
| 16 | 4-methyl-24-(2-methyl-2-propenyloxy)-5α-4-azacholan-3-one, |
| 16 | 24-allyloxy-4-methyl-5α-4-azacholan-3-one, |
| 13 | 17-(p-acetamido)phenoxymethyl)-4-methyl-5α-4-azaandrostan-3-one, |
| 26 | 24-((4-acetyl)phenylaminocarbonylmethoxy)-4-methyl-5α-4-azacholan-3-one. |

The following compounds are also encompassed by the instant invention. They can be prepared, using the appropriate starting materials, according to the procedures described in the noted examples, below.

| Prepared by Example | |
|---|---|
| 11 | 17β-(4-methoxyphenoxy)-4-methyl-4-aza-5α-androstan-3-one (mp 145–148° C.) |
| 26 | 17β-(1-adamantylaminocarbonylmethoxy)-4-aza-5α-androstan-3-one (mp 272–274° C.) |
| 26 | 17β-(2,2-dimethylethylaminocarbonylmethoxy)-4-aza-5α-androstan-3-one (mp 257–259° C.) |
| 26 | 17β-(2-hydroxyethylaminocarbonylmethoxy)-4-aza-5α-androstan-3-one (mp 213–214° C.) |
| 26 | 17β-(N,N-diisopropylacetamidoxy)-4-aza-5α-androstan-3-one (mp 235–237° C.) |
| 11 | 17β-(2-cyanophenoxy)-4-methyl-4-aza-5α-androstan-3-one (mp 175–177° C.) |
| 10 | 17β-(4-nitrophenoxy)-4-an-5α-androstan-3-one (mp 280–282° C.) |
| 10 | 17β-(2-nitrophenoxy)-4-aza-5α-androstan-3-one (mp 263.5–265° C.) |
| 14 | 17β-(2-carboxamidophenoxy)-4-methyl-4-aza-5α-androstan-3-one (mp 296–298° C.) |
| 10 | 17β-(2-nitrophenoxy)-4-methyl-4-aza-5α-androstan-3-one (mp 233–236° C.) |
| 11 | 17β-(3-cyanophenoxy)-4-methyl-4-aza-5α-androstan-3-one (mp 122–125° C.) |
| 11 | 17α-(4-cyanophenoxy)-4-methyl-4-aza-5α-androstan-3-one |

-continued

| Prepared by Example | |
|---|---|
| | (mp 196–199° C.) |
| 14 | 17β-(3-carboxamidophenoxy)-4-methyl-4-aza-5α-androstan-3-one (mp 255–258° C.) |
| 16 | 17β-{4-(N,N-dimethylcarbamoyl)-phenoxy}-4-methyl-4-aza-5α-androstan-3-one (mp 192–195° C.) |

BIOLOGICAL ASSAYS

Preparation of Human prostatic and scalp 5α-reductases.

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500xg for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase assay.

The reaction mixture contained in a final volume of 100 μl is: 40 mM buffer (human scalp, potassium phosphate, pH 6.5; human prostatic 5α-reductase, sodium citrate, pH 5.5), 0.3–10 μM $^{14}$C-T (or $^3$H-T) ("T" stands for testosterone), 1 mM DTT, and 500 μM NADPH. Typically, the assay was initiated by the addition of 50–100 μg prostatic homogenate or 75–200 μg scalp homogenate and incubated at 37° C. After 10–50 min the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendoff microfuge. The organic layer was subjected to normal phase HPLC (10 cm Whatman partisil 5 silica column equilibrated in 1 ml/min 70 % cyclohexane: 30 % ethyl acetate; retention times: DHT, 6.8–7.2 min; androstanediol, 7.6–8.0 min; T, 9.1–9.7 min). The HPLC system consisted of a Waters Model 680 Gradient System equipped with a Hitachi Model 655A autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Stumptail Macaque Protocol

The following protocol is utilized with the stumptail macaque monkey to demonstrate the effect of compounds of the present invention for promoting hair growth.

Twenty-one male stumptail macaque monkeys of species *Macaca speciosa* are assigned to vehicle control and drug treatment groups on the basis of baseline hair weight data. This assignment procedure is necessary to insure that the average baseline hair growth for each control and experimental group is comparable. The control and drug treatment groups are as follows:

1. Topical 50:30:20 vehicle (N=6)
2. Oral 5α-reductase and topical 50:30:20 vehicle (N=5)
3. Oral placebo (N= 5)
4. 5α-reductase in vehicle (N=5)

The vehicle consists of 50% propylene glycol, 30% ethanol and 20% water. A 100 mM concentration of topical 5α-reductase is formulated in this vehicle. The same 5α-reductase is administered as an oral dose of 0.5 mg per monkey. Immediately prior to the dosing phase of the study, hair is removed from a 1 inch square area (identified by four tattoos) in the center of the balding scalp. This hair collection is the baseline hair growth determination prior to the beginning of treatment. Approximately 250 μL of vehicle and 5α-reductase in vehicle is prepared and topically administered to the tattooed area of the scalp. The selected 5α-reductase and placebo is ingested by the monkeys at the same time as the topical doses are administered. The monkeys are dosed once per day, seven days per week for twenty weeks.

At four week intervals throughout the dosing phase of the study, each monkey is shaved and the hair is collected and weighed. The body weight data (at baseline and during assay) is analyzed by the nonparametric Wilcoxon rank-sum test. Differences are significant at p<0.05. Hair weight data at each week collection for vehicle, placebo and treatment groups are expressed as the change from baseline. Statistical analysis is performed on the rank of the data to show overall differences among groups at each four week collection.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of formula I

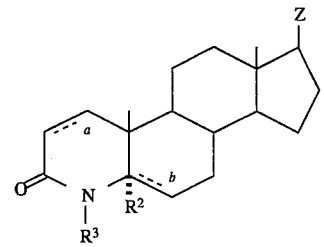

wherein "a" and "b" are both single bonds and $R^2$ is hydrogen, or "a" is a double bond, "b" is a single bond and $R^2$ is hydrogen, or "a" is a single bond, "b" is a double bond and $R^2$ is absent;

Z is —$XR^4$, or —$(CHR^1)_n$-$XR^4$;

n is an integer selected from 1 to 10;

X is —O— or —S(O)$_p$—, wherein p is zero, 1 or 2;
R$^1$ is
—H, aryl, or —C$_{1-3}$alkyl unsubstituted or substituted with aryl and when n is greater than 1, R$^1$ can be the same or different at each occurrence;
R$^3$ is
—H, methyl, ethyl, —OH, —NH$_2$ or —SCH$_3$;
R$^4$ is
(1) —C$_{1-20}$alkyl, unsubstituted or substituted with one or two of:
 (a) —OH,
 (b) halo,
 (c) —C$_{1-8}$alkoxy,
 (d) —C$_{1-10}$alkenyl,
 (e) —CONR$^5$R$^5$, wherein R$^5$ is independently
  (i) —H,
  (ii) —C$_{1-8}$alkyl unsubstituted or substituted with one of R$^7$, aryl or heterocycle, the aryl being unsubstituted or substituted with one of R$^7$ or R$^9$,
  (iii) aryl unsubstituted or substituted with one or two of R$^7$ or R$^9$, or
  (iv) heterocycle, unsubstituted or substituted with one of R$^7$ or R$^9$
 (f) —COOR$^6$, wherein R$^6$ is
  (i) —H,
  (ii) —C$_{1-8}$alkyl unsubstituted or substituted with one of R$^7$ or aryl, the aryl being unsubstituted or substituted with one of R$^7$ or R$^9$, or
  (iii) aryl, unsubstituted or substituted with one of R$^7$ or R$^9$,
 (g) —S(O)$^p$-R$^5$, wherein p is defined above,
 (h) —N(R$^5$)$_2$,
 (i) aryl, unsubstituted or substituted with one of aryl, R$^7$ or R$^9$,
 (j) heterocycle, unsubstituted or substituted with one of R$^7$ or R$^9$,
 (k) —C$_{3-10}$cycloalkyl, unsubstituted or substituted with one of R$^7$ or R$^9$, or
 (l) —CONR$^8$-CO-NHR$^8$, wherein R$^8$ is —H, —C$_{1-8}$alkyl, benzyl or cyclohexyl,
(2) aryl, unsubstituted or substituted with one or two of aryl, R$^7$ or R$^9$, or
(3) heterocycle or —C$_{3-10}$cycloalkyl, either of which is unsubstituted or substituted with one of R$^7$ or R$^9$;
R$^7$ is
(1) —OH,
(2) —C$_{1-3}$alkoxy,
(3) —CN,
(4) —COOR$^6$,
(5) —C$_{1-8}$alkyl-COOR$^6$
(6) —NO$_2$,
(7) -halo, or
(8) amino, mono-C$_1$-C$_4$-alkylamino, or di-C$_1$-C$_4$-alkylamino;
R$^9$ is
(1) —C$_{1-8}$alkyl, unsubstituted or substituted with one or two or three of aryl or R$^7$,
(2) —CO-A, —C$_{1-8}$alkyl-CO-A, —NHCO-A, or —S(O)$_p$-A, wherein p is defined above and A is
 (a) —H,
 (b) —C$_{1-8}$alkyl unsubstituted or substituted with one of
  (i) —R$^7$, or
  (ii) aryl, unsubstituted or substituted with one of R$^7$, or (c) aryl, unsubstituted or substituted with one of R$^7$,
(3) —NHCO-heterocycle,
(4) —N(R$^{10}$)$_2$ or —CON(R$^{10}$)$_2$ wherein R$^{10}$ is independently heterocycle, or —A,
(5) —NHCO-(CH$_2$)$_q$—CO-Q, wherein q is an integer from 1 to 4, and Q is —N(R$^{10}$)$_2$ or —OR$^{10}$;
aryl is phenyl or naphthyl;
heterocycle is
piperidinyl, 2-oxopiperidinyl, 2-oxopyrrolodinyl, pyrrolyl, 4-piperidonyl, pyrrolidinyl, pyrazolyl, pyrazolidinyl, imidazolyl, imidazolinyl, imidazolidinyl, pyridyl, oxazolyl, oxazolidinyl, isoxazolyl, isoxazolidinyl, thiazolyl, thiazolidinyl, isothiazolyl, quinuclidinyl, isothiazolidinyl, thiadiazolyl, benzopyranyl, benzothiazolyl, benzoxazolyl, furyl, tetrahydrofuryl, tetrahydropyranyl, thienyl or benzothienyl, with the proviso that when Z is —OR$^4$, R$^3$ is —H, "a" is a single bond and "b" is a single or double bond, R$^4$ is not isopentyl; or a pharmaceutically acceptable salt or ester thereof, wherein the ester is acetate, maleate or pivaloyloxymethyl.

2. The compound of claim 1 having structural formula II

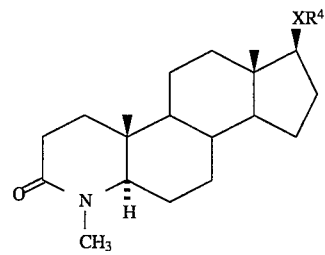

3. The compound of claim 2 wherein R$^4$ is —C$_{1-20}$ alkyl, unsubstituted or substituted with one or two of
—OH, halo, —C$_{1-8}$alkoxy, —C$_{1-6}$alkenyl, —S(O)$_p$—R$^5$, —N(R$^5$)$_2$, aryl unsubstituted or substituted with one of aryl, R$^7$ or R$^9$, heterocycle unsubstituted or substituted with one of R$^7$ or R$^9$, or —C$_{3-10}$ cycloalkyl unsubstituted or substituted with one of R$^7$ or R$^9$.

4. The compound of claim 2 wherein R$^4$ is —C$_{1-20}$ alkyl substituted with —CONR$^5$R$^5$, —COOR$^6$ or —CONR$^8$CONHR$^8$.

5. The compound of claim 2 wherein R$^4$ is aryl unsubstituted or substituted with one or two of aryl, R$^7$ or R$^9$;
heterocycle unsubstituted or substituted with one of R$^7$ or R$^9$; or
—C$_{3-10}$ cycloalkyl unsubstituted or substituted with one of R$^7$ or R$^9$.

6. The compound of claim 1 having structural formula III

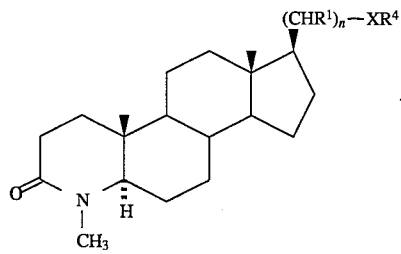

7. The compound of claim 6 wherein R$^4$ is —C$_{1-20}$ alkyl, unsubstituted or substituted with one or two of
—OH, halo, —C$_{1-8}$alkoxy, —C$_{1-6}$alkenyl, —S(O)$_p$-R$^5$, —N(R$^5$)$_2$, aryl unsubstituted or substituted with one or more of aryl, R$^7$ or R$^9$, heterocycle unsubstituted or substituted with one of R$^7$ or R$^9$, or —C$_{3-10}$ cycloalkyl unsubstituted or substituted with one of R$^7$ or R$^9$.

8. The compound of claim 6 wherein $R^4$ is $-C_{1-20}$ alkyl substituted with $-CONR^5R^5$, $-COOR^6$ or $-CONR^8CONHR^8$.

9. The compound of claim 6 wherein $R^4$ is aryl unsubstituted or substituted with one or two of aryl, $R^7$ or $R^9$;

heterocycle unsubstituted or substituted with one of $R^7$ or $R^9$; or $-C_{3-10}$ cycloalkyl unsubstituted or substituted with one of $R^7$ or $R^9$.

10. A compound selected from the group consisting of:

20-(methoxymethyl)-4-methyl-5α-4-azapregnan-3-one,
17-(carbobenzyloxymethoxymethyl)-4-methyl-5α-4-azaandrostan-3-one,
5α-4-azaandrostan-3-on-17β-yloxy-N-(4-acetylphenyl)acetamide,
17α-thiophenoxy-4-methyl-5α-4-azaandrostan-3-one,
17-(methoxymethyl)-4-methyl-5α-4-azaandrostan-3-one,
17-(ethylthiomethyl)-4-methyl-5α-4-azaandrostan-3-one,
17-(carboxymethoxymethyl)-4-methyl-5α-4-azaandrostan-3-one,
17-(carboethoxymethoxymethyl)-4-methyl-5α-4-azaandrostan-3-one,
17-(carbobenzyloxymethoxymethyl)-4-methyl-5α-4-azaandrostan-3-one,
17-(diphenylmethoxymethyl)-4-methyl-5α-4-azaandrostan-3-one,
20-(diphenylmethoxy)4-methyl-5α-4-azapregnan-3-one,
20-(methoxy)4-methyl-5α-4-azapregnan-3-one,
20-(methoxymethyl)-4-methyl-5α-4-azapregnan-3-one,
20-(diphenylmethoxymethyl)-4-methyl-5α-4-azapregnan-3-one,
20-(ethylthiomethyl)-4-methyl-5α-4-azapregnan-3-one,
20-(isopropylthiomethyl)-4-methyl-5α-4-azapregnan-3-one,
ethyl 4-methyl-5α-4-azaandrostan-3-on-17β-yloxyacetate,
diphenylmethyl 4-methyl-5α-4-azaandrostan-3-on-17β-yloxyacetate,
4-methyl-5α-4-azaandrostan-3-on-17β-yloxy-N-(3,4-dichlorobenzyl)acetamide,
4-methyl-5α-4-azaandrostan-3-on-17β-yloxy-N-phenylacetamide,
4-methyl-5α-4-azaandrostan-3-on-17β-yloxyacetic acid,
4-methyl-5α-4-azaandrostan-3-on-17β-yloxy-N-(4-acetylphenyl)acetamide,
4-methyl-5α-4-azaandrostan-3-on-17β-yloxyacetamide,
17β-(4-biphenyloxy)-4-methyl-5α- 4-azaandrostan-3-one,
17β-(2,4-dinitrophenoxy)-4-methyl-5α- 4-azaandrostan-3-one,
4-methyl-17α-phenoxy-5α-4-azaandrostan-3-one,
17α-(4-biphenyloxy)-4-methyl-5α-4-azaandrostan-3-one,
17β-diphenylmethoxy-4-methyl-5α-4-azaandrostan-3-one,
4-methyl-17α-thiophenoxy-5α-4-azaandrostan-3-one,
4-methyl-17α-phenylsulfonyl-5α-4-azaandrostan-3-one,
4-methyl-17α-phenylsulfinyl-5α-4-azaandrostan-3-one (isomer a),
4-methyl-17α-phenylsulfinyl-5α-4-azaandrostan-3-one (isomer b),
4-methyl-17β-(4-nitrophenoxy)-5α-4-azaandrostan-3-one,
17β-(4-aminophenoxy)-4-methyl-5α-4-azaandrostan-3-one hydrochloride,
17β-(4-acetamidophenoxy)-4-methyl-5α-4-azaandrostan-3-one,
17β-(4-cyanophenoxy)-4-methyl-5α-4-azaandrostan-3-one,
17β-(4-carboxamidophenoxy)-4-methyl-5α-4-azaandrostan-3-one,
17β-methyleneoxy-[N-cyclohexyl-N-(N-cyclohexyl-carbamoyl)carbamoyl]4-methyl-5α-4-azaandrostan-3-one,
4-methyl-17β-(3-pyridyl)oxy-5α-4-azaandrostan-3-one,
4-methyl-17β-(2-pyridyl)methoxy-5α-4-azaandrostan-3-one,
17β-benzyloxy-4-methyl-5α-4-azaandrostan-3-one,
ethyl 5α-4-azaandrostan-3-on-17β-yloxyacetate,
5α-4-azaandrostan-3-on-17β-yloxyacetic acid,
5α-4-azaandrostan-3-on-17β-yloxy-N-phenylacetamide,
5α-4-azaandrostan-3-on-17β-yloxy-N-(4-acetylphenyl)acetamide,
diphenylmethyl 5α-4-azaandrostan-3-on-17β-yloxyacetate,
17β-methyleneoxy-[N-cyclohexyl-N-(N-cyclohexyl-carbamoyl)carbamoyl]- 5α-4-azaandrostan-3-one,
5α-4-azaandrostan-3-on-17β-yloxy-N-[4-( 1(RS)-hydroxyethyl)phenyl]acetamide,
5α-4-azaandrostan-3-on-17β-yloxy-N-( 4-t-butylphenyl)acetamide,
17β-methyleneoxy-[N-isopropyl-N-(N-isopropyl-carbamoyl)carbamoyl]- 5α-4-azaandrostan-3-one,
17-(4-methylpentyloxy)4-methyl-5α- 4-azaandrostan-3-one,
17-hexyloxy-4-methyl-5α-4-azaandrostan-3-one,
4-methyl-17-propyloxy-5α-4-azaandrostan-3-one,
4-methyl-17-undecyloxy-5α-4-azaandrostan-3-one,
17-allyloxy-4-methyl-5α-4-azaandrostan-3-one,
17-allyloxy-4-methyl-4-azaandrost-5-en-3-one, and
17-hexyloxy-4-methyl-4-azaandrost-5-en-3-one, ps or a pharmaceutically acceptable salt or ester thereof.

11. A compound selected from the group consisting of:

4-methyl-17-(3-methylbutyloxymethyl)- 5α-4-azaandrostan-3-one,
4-methyl-20-(3-methylbutyloxymethyl)-5α-4-azapregnan-3 -one,
4-methyl-17-(N-phenylcarboxamidomethoxymethyl)-5α-4-azaandrostan- 3-one,
4-methyl-17-(p-Nitrophenoxymethyl)-4-methyl-5α-4-azaandrostan-3-one,
17-(p-(dimethylamino)phenoxymethyl)-4-methyl-5α-4-azaandrostan-3-one,
24-(isopropylthio)-4-methyl-5α-4-azacholan-3-one,
4-methyl-17-(p-trimethylammonium)phenoxymethyl)-5α-4-azaandrostan-3-one iodide,
17-(3-(isopropylthio)propyl)-4-methyl-5α-4-azaandrostan-3-one,
17-(allyloxymethyl)-4-methyl-5α-4-azaandrostan-3-one,
4-methyl-17-(n-propyloxymethyl)-5α-4-azaandrostan-3-one,
20-(allyloxymethyl)-4-methyl-5α-4-azapregnan-3-one, N-phenyl 4-methyl-5α-22-oxa-3-oxo-4-azacholanamide, N-(4-acetylphenyl) 4-methyl-5α-22-oxa-3-oxo-4-azacholanamide, 4-methyl-24-(2-methyl-2-propenyloxy)-5α-4-azacholan-3-one, 24-allyloxy-4-methyl-5α-4-azacholan-3-one, 17-(p-acetamido)phenoxymethyl)-4-methyl-5α-4-azaandrostan-3-one, 24-((4-acetyl)phenylaminocarbonylmethoxy)-4-methyl-5α-4-azacholan-3-one, 17β-(4-methoxyphenoxy)-4-methyl-4-aza-5α-androstan-3-one, 17β-(1-adamantylaminocarbonylmethoxy)-4-aza-5α-androstan-3-one, 17β-(2,2-dimethylethylaminocarbonylmethoxy)-4-aza-5α-androstan-3-one, 17β-(2-hydroxyethylaminocarbonylmethoxy)-4-aza-5α-androstan-3-one, 17β-(N,N-diisopropylacetamidoxy)-4-aza-5α-androstan-3-one, 17β-(2-cyanophenoxy)-4-methyl-4-aza-5α-androstan-3-one, 17β-(4-nitrophenoxy)-4-aza-5α-androstan-3-one, 17β-(2-nitrophenoxy)-4-aza-5α-androstan-3-one, 17β-(2-carboxamidophenoxy)-4-methyl-4-aza-5α-androstan-3-one, 17β-(2-nitrophenoxy)-4-methyl-4-aza-5α-androstan-3-one, 17β-(3-cyanophenoxy)-4-methyl-4-aza-5α-androstan-3-one, 17α-(4-cyanophenoxy)4-methyl-4-aza-5α-androstan-3-one, 17β-(3-carboxamidophenoxy)-4-methyl-4-aza-5α-androstan-3-one, and 17β-{4-(N,N-dimethylcarbamoyl)-phenoxy}- 4-methyl-4-aza-5α-androstan-3-one, or a pharmaceutically acceptable salt or ester thereof.

12. A pharmaceutical composition comprising 0.5 to 1000 mg of a compound of claim 1 in a pharmaceutically acceptable carder therefor.

* * * * *

UNITED STATES PATENT AND TRADEMARK OFFICE
CERTIFICATE OF CORRECTION

PATENT NO. : 5,536,727

DATED : July 16, 1996

INVENTOR(S) : Bruce E. Witzel et al.

It is certified that error appears in the above-identified patent and that said Letters Patent is hereby corrected as shown below:

In Claim 1, at Column 35, line 31, amend "-S(O)$^p$-R$^5$-" to read -- -S(O)$_p$-R$^5$ --.

In Claim 10, at Column 38, line 45, after "17-hexyloxy-4-methyl-4-azaandrost-5-en-3-one," delete -- ps --.

In Claim 12, at Column 40, line 22, delete "carder" and substitute therefor -- carrier --.

Signed and Sealed this

Twenty-fourth Day of September, 1996

Attest:

BRUCE LEHMAN

*Attesting Officer*  *Commissioner of Patents and Trademarks*